US011491217B2

(12) United States Patent
Kim

(10) Patent No.: US 11,491,217 B2
(45) Date of Patent: Nov. 8, 2022

(54) CHIMERIC VIRUSES ENCODING MUTANT ZIKA VIRUS ENVELOPE GLYCOPROTEINS

(71) Applicant: Emory University, Atlanta, GA (US)

(72) Inventor: Baek Kim, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 32 days.

(21) Appl. No.: 16/770,164

(22) PCT Filed: Dec. 6, 2018

(86) PCT No.: PCT/US2018/064201
§ 371 (c)(1),
(2) Date: Jun. 5, 2020

(87) PCT Pub. No.: WO2019/113285
PCT Pub. Date: Jun. 13, 2019

(65) Prior Publication Data
US 2021/0162035 A1     Jun. 3, 2021

Related U.S. Application Data

(60) Provisional application No. 62/595,510, filed on Dec. 6, 2017.

(51) Int. Cl.
| | | |
|---|---|---|
| *A61K 39/12* | (2006.01) | |
| *C07K 14/005* | (2006.01) | |
| *C12N 7/00* | (2006.01) | |
| *A61K 39/00* | (2006.01) | |

(52) U.S. Cl.
CPC ............ *A61K 39/12* (2013.01); *C07K 14/005* (2013.01); *C12N 7/00* (2013.01); *A61K 2039/5254* (2013.01); *A61K 2039/5258* (2013.01); *C12N 2770/24121* (2013.01); *C12N 2770/24122* (2013.01); *C12N 2770/24123* (2013.01); *C12N 2770/24134* (2013.01)

(58) Field of Classification Search
CPC .......... A61K 39/12; C12N 2770/24134; C12N 2770/24121
See application file for complete search history.

(56) References Cited

U.S. PATENT DOCUMENTS

| | | | | |
|---|---|---|---|---|
| 6,696,281 B1 * | 2/2004 | Chambers | ............ | C07K 14/005 435/235.1 |
| 10,588,956 B2 | 3/2020 | Sumathy | | |
| 2017/0014502 A1 | 1/2017 | Sumathy | | |

FOREIGN PATENT DOCUMENTS

| | | |
|---|---|---|
| WO | 2010085358 | 7/2010 |
| WO | 2012003320 | 1/2012 |
| WO | 2014016360 | 1/2014 |
| WO | 2016209805 | 12/2016 |
| WO | 2017147458 | 8/2017 |
| WO | WO 2017/147458 A1 * | 8/2017 |
| WO | 2018060771 | 4/2018 |

OTHER PUBLICATIONS

Guirakhoo, F., et al., Jun. 2000, Recombinant chimeric yellow fever-dengue type 2 virus is immunogenic and protective in non-human primates, J. Virol. 74(12):5477-5485.*
Larocca, R. A., et al., Aug. 2016, Vaccine protection against Zika virus from Brazil, Nature 536:474-489.*
Yun, S.-I., et al., Jul./Aug. 2016, Complete Genome Sequences of Three Historically Important, Spatiotemporally Distinct, and Genetically Divergent Strains of Zika Virus: MR-766, PG-740, and PRVABC-59, Genome Announcements 4(4):e00800-16, pp. 1-4.*
Guirakhoo, F., et al., Aug. 2001, Construction, Safety, and Immunogenicity in Nonhuman Primates of a Chimeric Yellow Fever-Dengue Virus Tetravalent Vaccine, J. Virol. 75(16):7290-7304.*
Arroyo et al. Molecular Basis for Attenuation of Neurovirulence of a Yellow Fever Virus/Japanese Encephalitis Virus Chimera Vaccine (ChimeriVax-JE) Journal of Virology, 2001, vol. 75, No. 2, p. 934-942.
Cohen, The race for a Zika vaccine is on, Science, 2016 • vol. 351, Issue 6273, 543-4.
Dawes et al. Research and development of Zika virus vaccines, npj Vaccines (2016) 1, 16007.
Giel-Moloney et al. Chimeric yellow fever 17D-Zika virus (ChimeriVax-Zika) as a live attenuated Zika virus vaccine, Sci Rep 8, 13206 (2018).
Zhang et al. Structures of immature flavivirus particles, The EMBO Journal vol. 22 No. 11 pp. 2604-2613, 2003.
Chin et al. Japanese B Encephalitis: An Overview of the Disease and Use of Chimerivax-JE as a Preventative Vaccine, Infect Dis Ther (2013) 2:145-158.
Dudley et al. A rhesus macaque model of Asian-lineage Zika virus infection, Nat Commun, 2016, 7:12204.
Lazear et al. A Mouse Model of Zika Virus Pathogenesis, Cell Host Microbe. 2016, 19(5): 720-730.

(Continued)

*Primary Examiner* — Jeffrey S Parkin
(74) *Attorney, Agent, or Firm* — Emory Patent Group

(57) ABSTRACT

The present disclosure relates to Zika vaccines. In certain embodiments, this disclosure relates to vaccine compositions for use in methods of protecting a human subject against Zika disease or infection, wherein said composition comprises a vaccinal for Zika such as a live attenuated or inactivated chimeric Zika virus; live attenuated Zika virus; an inactivated Zika virus; a replication-defective pseudo-infectious Zika virus; a Zika virus-like particle (VLP), a Zika protein or combinations thereof. In certain embodiments, the Zika vaccinal comprises or encodes altered polypeptide sequences disclosed herein.

15 Claims, 2 Drawing Sheets
Specification includes a Sequence Listing.

(56) References Cited

OTHER PUBLICATIONS

Monath et al. A live, attenuated recombinant West Nile virus vaccine, PNAS, 2006, 103(17):6694-6699.
Rossi et al. Characterization of a Novel Murine Model to Study Zika Virus, Am. J. Trop. Med. Hyg., 94(6), 2016, pp. 1362-1369.

* cited by examiner

ZKV-YFV Attenuated Vaccine Construct

T7 P — 5' NCS — C — ZKV (Pre-M, M and E (or E*)) — YFV NS proteins — 3' NCS — HDVr

FIG. 1

```
Q   1  IRCIGVSNRD FVEGMSGGTW VDVVLEHGGC VTVMAQDKPT VDIELVTTTV SNMAEVRSYC  60
       IRCIGVSNRD FVEGMSGGTW VDVVLEHGGC VTVMAQDKPT VDIELVTTTV SNMAEVRSYC
S   1  IRCIGVSNRD FVEGMSGGTW VDVVLEHGGC VTVMAQDKPT VDIELVTTTV SNMAEVRSYC  60

Q  61  YEASISDMAS DSRCPTQGEA YLDKQSDTQY VCKRTLVDRG WGNGCGFFGK GSLVTCAKFA 120
       YEASISDMAS DSRCPTQGEA YLDKQSDTQY VCKRTLVDRG WGNGCG FGK GSLVTCAKFA
S  61  YEASISDMAS DSRCPTQGEA YLDKQSDTQY VCKRTLVDRG WGNGCGLFGK GSLVTCAKFA 120

Q 121  CSKKMTGKSI QPENLEYKIM LSVHGSQHSG MIVNDTGHET DENRAKVEIT PNSPRVEATL 180
       CSKKMTGKSI QPENLEY+IM LSVHGSQHSG MIVNDTGHET DENRAKVEIT PNSPR EATL
S 121  CSKKMTGKSI QPENLEYRIM LSVHGSQHSG MIVNDTGHET DENRAKVEIT PNSPRAEATL 180

Q 181  GGFGSLGLDC EPRTGLDFSD LYYLTMNNKH WLVHKEWFHD IPLPWHAGAD TGTPHWNNKE 240
       GGFGSLGLDC EPRTGLDFSD LYYLTMNNKH WLVHKEWFHD IPLPWHAGAD TGTPHWNNKE
S 181  GGFGSLGLDC EPRTGLDFSD LYYLTMNNKH WLVHKEWFHD IPLPWHAGAD TGTPHWNNKE 240

SEQ ID NO :1
Q 241  ALVEFKDAHA KRQTVVVLGS QEGAVHHALA GAIEAEMDGA KGMLSSGHLK CRLKMDKLRL 300
       ALVEFKDAHA KRQTVVVLGS QEGAVH ALA GAIEAEMDGA KG LSSGHLK CRLKMDKLRL
                                                             SEQ ID NO: 12
S 241  ALVEFKDAHA KRQTVVVLGS QEGAVHTALA GAIEAEMDGA KGRLSSGHLK CRLKMDKLRL 300
                                                             SEQ ID NO: 2
```

FIG. 2

SEQUENCE LISTING

<160> NUMBER OF SEQ ID NOS: 12

<210> SEQ ID NO 1

<211> LENGTH: 300
<212> TYPE: PRT
<213> ORGANISM: Artificial
<220> FEATURE:
<223> OTHER INFORMATION: Synthetic construct

<400> SEQUENCE: 1

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Phe Phe Gly Lys Gly Ser
            100                 105                 110

Leu Val Thr Cys Ala Lys Phe Ala Cys Ser Lys Lys Met Thr Gly Lys
        115                 120                 125

Ser Ile Gln Pro Glu Asn Leu Glu Tyr Lys Ile Met Leu Ser Val His
    130                 135                 140

Gly Ser Gln His Ser Gly Met Ile Val Asn Asp Thr Gly His Glu Thr
145                 150                 155                 160

Asp Glu Asn Arg Ala Lys Val Glu Ile Thr Pro Asn Ser Pro Arg Val
                165                 170                 175

Glu Ala Thr Leu Gly Gly Phe Gly Ser Leu Gly Leu Asp Cys Glu Pro
            180                 185                 190

Arg Thr Gly Leu Asp Phe Ser Asp Leu Tyr Tyr Leu Thr Met Asn Asn
        195                 200                 205

Lys His Trp Leu Val His Lys Glu Trp Phe His Asp Ile Pro Leu Pro
    210                 215                 220

Trp His Ala Gly Ala Asp Thr Gly Thr Pro His Trp Asn Asn Lys Glu
225                 230                 235                 240

Ala Leu Val Glu Phe Lys Asp Ala His Ala Lys Arg Gln Thr Val Val
                245                 250                 255

Val Leu Gly Ser Gln Glu Gly Ala Val His His Ala Leu Ala Gly Ala
            260                 265                 270

Leu Glu Ala Glu Met Asp Gly Ala Lys Gly Met Leu Ser Ser Gly His
        275                 280                 285

Leu Lys Cys Arg Leu Lys Met Asp Lys Leu Arg Leu
    290                 295                 300
```

<210> SEQ ID NO 2
<211> LENGTH: 300
<212> TYPE: PRT
<213> ORGANISM: Artificial
<220> FEATURE:
<223> OTHER INFORMATION: Synthetic construct

<400> SEQUENCE: 2

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
```

```
                20                  25                  30
Val Met Ala Gln Asp Lys Pro Thr Val Asp Ile Glu Leu Val Thr Thr
            35                  40                  45
Thr Val Ser Asn Met Ala Glu Val Arg Ser Tyr Cys Tyr Glu Ala Ser
        50                  55                  60
Ile Ser Asp Met Ala Ser Asp Ser Arg Cys Pro Thr Gln Gly Glu Ala
65                  70                  75                  80
Tyr Leu Asp Lys Gln Ser Asp Thr Gln Tyr Val Cys Lys Arg Thr Leu
                85                  90                  95
Val Asp Arg Gly Trp Gly Asn Gly Cys Gly Leu Phe Gly Lys Gly Ser
            100                 105                 110
Leu Val Thr Cys Ala Lys Phe Ala Cys Ser Lys Lys Met Thr Gly Lys
        115                 120                 125
Ser Ile Gln Pro Glu Asn Leu Glu Tyr Arg Ile Met Leu Ser Val His
    130                 135                 140
Gly Ser Gln His Ser Gly Met Ile Val Asn Asp Thr Gly His Glu Thr
145                 150                 155                 160
Asp Glu Asn Arg Ala Lys Val Glu Ile Thr Pro Asn Ser Pro Arg Ala
                165                 170                 175
Glu Ala Thr Leu Gly Gly Phe Gly Ser Leu Gly Leu Asp Cys Glu Pro
            180                 185                 190
Arg Thr Gly Leu Asp Phe Ser Asp Leu Tyr Tyr Leu Thr Met Asn Asn
        195                 200                 205
Lys His Trp Leu Val His Lys Glu Trp Phe His Asp Ile Pro Leu Pro
    210                 215                 220
Trp His Ala Gly Ala Asp Thr Gly Thr Pro His Trp Asn Asn Lys Glu
225                 230                 235                 240
Ala Leu Val Glu Phe Lys Asp Ala His Ala Lys Arg Gln Thr Val Val
                245                 250                 255
Val Leu Gly Ser Gln Glu Gly Ala Val His Thr Ala Leu Ala Gly Ala
            260                 265                 270
Leu Glu Ala Glu Met Asp Gly Ala Lys Gly Arg Leu Ser Ser Gly His
        275                 280                 285
Leu Lys Cys Arg Leu Lys Met Asp Lys Leu Arg Leu
    290                 295                 300

<210> SEQ ID NO 3
<211> LENGTH: 11000
<212> TYPE: DNA
<213> ORGANISM: Artificial
<220> FEATURE:
<223> OTHER INFORMATION: Synthetic construct

<400> SEQUENCE: 3
taatacgact cactatagag taaatcctgt gtgctaattg aggtgcattg gtctgcaaat    60
cgagttgcta ggcaataaac acatttggat taattttaat cgttcgttga gcgattagca   120
gagaactgac cagaacatgt ctggtcgtaa agctcaggga aaaccctggg cgtcaatat   180 ggtacgacga ggagttcgct ccttgtcaaa caaaataaaa caaaaaacaa aacaaattgg   240
aaacagacct ggaccttcaa gaggtgttca aggatttatc ttttttcttt tgttcaacat   300
tttgactgga aaaagatcag cagcccacct aaagaggttg tggaaaatgc tggacccaag   360
acaaggcttg gctgttctaa ggaaagtcaa gagagtggtg gccagtttga tgagaggatt   420
gtcctcaagg aaacgccgtt cccatgatgt tctgactgtg caattcctaa ttttgggaat   480
```

-continued

```
gctgttgatg acgggtggag tgaccttggt gcggcgtggg agcgcttact atatgtactt    540
ggacagaaac gatgctgggg aggccatatc ttttccaacc acattgggga tgaataagtg    600
ttatatacag atcatggatc ttggacacat gtgtgatgcc accatgagct atgaatgccc    660
tatgctggat gaggggtgg aaccagatga cgtcgattgt tggtgcaaca cgacgtcaac     720
ttgggttgtg tacggaacct gccatcacaa aaaaggtgaa gcacggagat caagaagagc    780
tgtgacgctc ccctcccatt ccactaggaa gctgcaaacg cggtcgcaaa cctggttgga    840
atcaagagaa tacacaaagc acttgattag agtcgaaaat tggatattca ggaaccctgg    900
cttcgcgtta gcagcagctg ccatcgcttg gcttttggga agctcaacga gccaaaaagt    960
catatacttg gtcatgatac tgctgattgc cccggcatac agcatcaggt gcataggagt   1020
cagcaatagg gactttgtgg aaggtatgtc aggtgggact tgggttgatg ttgtcttgga   1080
acatggaggt tgtgtcaccg taatggcaca ggacaaaccg actgtcgaca tagagctggt   1140
tacaacaaca gtcagcaaca tggcggaggt aagatcctac tgctatgagg catcaatatc   1200
agacatggct tcggacagcc gctgcccaac acaaggtgaa gcctaccttg acaagcaatc   1260
agacactcaa tatgtctgca aaagaacgtt ggtggacaga ggctggggaa atggatgtgg   1320
acttttggc aaagggagcc tggtgacatg cgctaagttt gcatgctcca agaaaatgac    1380
cgggaagagc atccagccag agaatctgga gtaccggata atgctgtcag ttcatggctc   1440
ccagcacagt gggatgatcg ttaatgacac aggacatgaa actgatgaga atagagcgaa   1500
ggttgagata acgcccaatt caccaagagc cgaagccacc ctgggggggtt ttggaagcct   1560
aggacttgat tgtgaaccga ggacaggcct tgacttttca gatttgtatt acttgactat   1620
gaataacaag cattggttgg ttcacaagga gtggttccac gacattccat taccttggca   1680
cgctggggca gacaccggaa ctccacactg gaacaacaaa gaagcactgg tagagttcaa   1740
ggacgcacat gccaaaaggc aaactgtcgt ggttctaggg agtcaagaag gagcagttca   1800
cacggccctt gctggagctc tggaggctga atggatggt gcaaagggaa ggctgtcctc    1860
tggccacttg aaatgtcgcc tgaaaatgga taaacttaga ttgaagggcg tgtcatactc   1920
cttgtgtacc gcagcgttca cattcaccaa gatcccggct gaaacactgc acggacagt    1980
cacagtggag gtacagtacg caggggcaga tggaccctgc aaggttccag ctcagatggc   2040
ggtgacatg caaactctga ccccagttgg gaggttgata accgccaacc ccgtaatcac    2100
tgaaagcact gagaactcta agatgatgct ggaacttgat ccaccatttg gggactctta   2160
cattgtcata ggagtcgggg agaagaagat cacccaccac tggcacagga gtggcagcac   2220
cattggaaaa gcatttgaag ccactgtgag aggtgccaag agaatggcag tcttgggaga   2280
cacagcctgg gactttggat cagttggagg cgctctcaac tcattgggca agggcatcca   2340
tcaaattttt ggagcagctt tcaaatcatt gtttggagga atgtcctggt tctcacaaat   2400
cctcattgga acgttgctga tgtgttgggc tctgaacaca aagaatggat ctatttccct   2460
tatgtgcttg gccttagggg gagtgttgat cttcttatcc ctaggagttg gcgccgatca   2520
aggatgcgcc atcaactttg gcaagagaga gctcaagtgc ggagatggta tcttcatatt   2580
tagagactct gatgactggc tgaacaagta ctcatactat ccagaagatc tgtgaagct    2640
tgcatcaata gtgaaagcct cttttgaaga agggaagtgt ggcctaaatt cagttgactc   2700
ccttgagcat gagatgtgga gaagcagggc agatgagatc aatgccattt ttgaggaaaa   2760
cgaggtggac atttctgttg tcgtgcagga tccaaagaat gtttaccaga gaggaactca   2820
tccattttcc agaattcggg atggtctgca gtatggttgg aagacttggg gtaagaacct   2880
```

```
tgtgttctcc ccagggagga agaatggaag cttcatcata gatggaaagt ccaggaaaga    2940
atgcccgttt tcaaaccggg tctggaattc tttccagata gaggagtttg ggacgggagt    3000
gttcaccaca cgcgtgtaca tggacgcagt ctttgaatac accatagact gcgatggatc    3060
tatcttgggt gcagcggtga acggaaaaaa gagtgcccat ggctctccaa cattttggat    3120
gggaagtcat gaagtaaatg ggacatggat gatccacacc ttggaggcat tagattacaa    3180
ggagtgtgag tggccactga cacatacgat tggaacatca gttgaagaga gtgaaatgtt    3240
catgccgaga tcaatcggag gcccagttag ctctcacaat catatccctg gatacaaggt    3300
tcagacgaac ggaccttgga tgcaggtacc actagaagtg aagagagaag cttgcccagg    3360
gactagcgtg atcattgatg gcaactgtga tggacgggga aaatcaacca gatccaccac    3420
ggatagcggg aaagttattc ctgaatggtg ttgccgctcc tgcacaatgc cgcctgtgag    3480
cttccatggt agtgatgggt gttggtatcc catggaaatt aggccaagga aaacgcatga    3540
aagccatctg gtgcgctcct gggttacagc tggagaaata catgctgtcc cttttggttt    3600
ggtgagcatg atgatagcaa tggaagtggt cctaaggaaa agacagggac caaagcaaat    3660
gttggttgga ggagtagtgc tcttgggagc aatgctggtc gggcaagtaa ctctccttga    3720
tttgctgaaa ctcacagtgg ctgtgggatt gcatttccat gagatgaaca atggaggaga    3780
cgccatgtat atgcgcttga ttgctgcctt ttcaatcaga ccagggctgc tcatcggctt    3840
tgggctcagg accctatgga gccctcggga acgccttgtg ctgaccctag gagcagccat    3900
ggtggagatt gccttgggtg gcgtgatggg cggcctgtgg aagtatctaa atgcagtttc    3960
tctctgcatc ctgacaataa atgctgttgc ttctaggaaa gcatcaaata ccatcttgcc    4020
cctcatggct ctgttgacac ctgtcactat ggctgaggtg agacttgccg caatgttctt    4080
ttgtgccgtg gttatcatag gggtccttca ccagaatttc aaggacacct ccatgcagaa    4140
gactatacct ctggtggccc tcacactcac atcttacctg ggcttgacac aaccttttt    4200 gggcctgtgt gcatttctgg caacccgcat atttgggcga aggagtatcc cagtgaatga    4260
ggcactcgca gcagctggtc tagtgggagt gctggcagga ctggcttttc aggagatgga    4320
gaacttcctt ggtccgattg cagttggagg actcctgatg atgctggtta gcgtggctgg    4380
gagggtggat gggctagagc tcaagaagct tggtgaagtt tcatgggaag aggaggcgga    4440
gatcagcggg agttccgccc gctatgatgt ggcactcagt gaacaagggg agttcaagct    4500
gctttctgaa gagaaagtgc catgggacca ggttgtgatg acctcgctgg ccttggttgg    4560
ggctgccctc catccatttg ctcttctgct ggtccttgct gggtggctgt tcatgtcag    4620 gggagctagg agaagtgggg atgtcttgtg ggatattccc actcctaaga tcatcgagga    4680
atgtgaacat ctgaggatg ggatttatgg catattccag tcaaccttct tgggggcctc    4740
ccagcgagga gtgggagtgg cacagggagg ggtgttccac acaatgtggc atgtcacaag    4800
aggagctttc cttgtcagga atggcaagaa gttgattcca tcttgggctt cagtaaagga    4860
agaccttgtc gcctatggtg gctcatggaa gttggaaggc agatgggatg gagaggaaga    4920
ggtccagttg atcgcggctg ttccaggaaa gaacgtggtc aacgtccaga caaaaccgag    4980
cttgttcaaa gtgaggaatg ggggagaaat cggggctgtc gctcttgact atccgagtgg    5040
cacttcagga tctcctattg ttaacaggaa cggagaggtg attgggctgt acggcaatgg    5100
catccttgtc ggtgacaact ccttcgtgtc cgccatatcc cagactgagg tgaaggaaga    5160
aggaaaggag gagctccaag agatcccgac aatgctaaag aaaggaatga caactgtcct    5220
```

```
tgattttcat cctggagctg ggaagacaag acgtttcctc ccacagatct tggccgagtg   5280
cgcacggaga cgcttgcgca ctcttgtgtt ggcccccacc agggttgttc tttctgaaat   5340
gaaggaggct tttcacggcc tggacgtgaa attccacaca caggcttttt ccgctcacgg   5400
cagcgggaga gaagtcattg atgccatgtg ccatgccacc ctaacttaca ggatgttgga   5460
accaactagg gttgttaact gggaagtgat cattatggat gaagcccatt ttttggatcc   5520
agctagcata gccgctagag gttgggcagc gcacagagct agggcaaatg aaagtgcaac   5580
aatcttgatg acagccacac cgcctgggac tagtgatgaa tttccacatt caaatggtga   5640
aatagaagat gttcaaacgg acatacccag tgagccctgg aacacagggc atgactggat   5700
cctagctgac aaaaggccca cggcatggtt ccttccatcc atcagagctg caaatgtcat   5760
ggctgcctct ttgcgtaagg ctggaaagag tgtggtggtc ctgaacagga aaacctttga   5820
gagagaatac cccacgataa agcagaagaa acctgacttt atattggcca ctgacatagc   5880
tgaaatggga gccaaccttt gcgtggagcg agtgctggat tgcaggacgg cttttaagcc   5940
tgtgcttgtg gatgaaggga ggaaggtggc aataaaaggg ccacttcgta tctccgcatc   6000
ctctgctgct caaaggaggg ggcgcattgg gagaaatccc aacagagatg gagactcata   6060
ctactattct gagcctacaa gtgaaaataa tgcccaccac gtctgctggt tggaggcctc   6120
aatgctcttg gacaacatgg aggtgagggg tggaatggtc gccccactct atggcgttga   6180
aggaactaaa acaccagttt ccccctggtga aatgagactg agggatgacc agaggaaagt   6240
cttcagagaa ctagtgagga attgtgacct gcccgtttgg ctttcgtggc aagtggccaa   6300
ggctggtttg aagacgaatg atcgtaagtg gtgttttgaa ggccctgagg aacatgagat   6360
cttgaatgac agcggtgaaa cagtgaagtg cagggctcct ggaggagcaa agaagcctct   6420
gcgcccaagg tggtgtgatg aaagggtgtc atctgaccag agtgcgctgt ctgaatttat   6480
taagtttgct gaaggtagga ggggagctgc tgaagtgcta gttgtgctga gtgaactccc   6540
tgatttcctg gctaaaaaag gtggagaggc aatggatacc atcagtgtgt tcctccactc   6600
tgaggaaggc tctagggctt accgcaatgc actatcaatg atgcctgagg caatgacaat   6660
agtcatgctg tttatactgg ctggactact gacatcggga atggtcatct ttttcatgtc   6720
tcccaaaggc atcagtagaa tgtctatggc gatgggcaca atggccggct gtggatatct   6780
catgttcctt ggaggcgtca aacccactca catctcctat gtcatgctca tattctttgt   6840
cctgatggtg gttgtgatcc ccgagccagg gcaacaaagg tccatccaag acaaccaagt   6900 ggcataccte attattggca tcctgacgct ggtttcagcg gtggcagcca acgagctagg   6960
catgctggag aaaaccaaag aggacctctt tgggaagaag aacttaattc catctagtgc   7020
ttcaccctgg agttggccgg atcttgacct gaagccagga gctgcctgga cagtgtacgt   7080
tggcattgtt acaatgctct ctccaatgtt gcaccactgg atcaaagtcg aatatggcaa   7140
cctgtctctg tctggaatag cccagtcagc ctcagtcctt tctttcatgg acaaggggat   7200
accattcatg aagatgaata tctcggtcat aatgctgctg gtcagtggct ggaattcaat   7260
aacagtgatg cctctgctct gtggcatagg gtgcgccatg ctccactggt ctctcatttt   7320
acctggaatc aaagcgcagc agtcaaagct tgcacagaga agggtgttcc atggcgttgc   7380
cgagaaccct gtggttgatg ggaatccaac agttgacatt gaggaagctc ctgaaatgcc   7440
tgccctttat gagaagaaac tggctctata tctccttctt gctctcagcc tagcttctgt   7500
tgccatgtgc agaacgccct tttcattggc tgaaggcatt gtcctagcat cagctgcctt   7560
agggccgctc atagagggaa acaccagcct tctttggaat ggacccatgg ctgtctccat   7620
```

-continued

| | | | | | |
|---|---|---|---|---|---|
| gacaggagtc | atgaggggga | atcactatgc | ttttgtggga | gtcatgtaca | atctatggaa | 7680 |
| gatgaaaact | ggacgccggg | ggagcgcgaa | tggaaaaact | ttgggtgaag | tctggaagag | 7740 |
| ggaactgaat | ctgttggaca | agcgacagtt | tgagttgtat | aaaaggaccg | acattgtgga | 7800 |
| ggtggatcgt | gatacggcac | gcaggcattt | ggccgaaggg | aaggtggaca | ccggggtggc | 7860 |
| ggtctccagg | gggaccgcaa | agttaaggtg | gttccatgag | cgtggctatg | tcaagctgga | 7920 |
| aggtaggggtg | attgacctgg | ggtgtggccg | cggaggctgg | tgttactacg | ctgctgcgca | 7980 |
| aaaggaagtg | agtggggtca | aaggatttac | tcttggaaga | gacggccatg | agaaacccat | 8040 |
| gaatgtgcaa | agtctgggat | ggaacatcat | caccttcaag | gacaaaactg | atatccaccg | 8100 |
| cctagaacca | gtgaaatgtg | acacccttt | gtgtgacatt | ggagagtcat | catcgtcatc | 8160 |
| ggtcacagag | gggaaagga | ccgtgagagt | tcttgatact | gtagaaaaat | ggctggcttg | 8220 |
| tggggttgac | aacttctgtg | tgaaggtgtt | agctccatac | atgccagatg | ttctcgagaa | 8280 |
| actgaattc | ctccaaagga | ggtttggcgg | aacagtgatc | aggaaccctc | tctccaggaa | 8340 |
| ttccactcat | gaaatgtact | acgtgtctgg | agcccgcagc | aatgtcacat | ttactgtgaa | 8400 |
| ccaaacatcc | cgcctcctga | tgaggagaat | gaggcgtcca | actggaaaag | tgaccctgga | 8460 |
| ggctgacgtc | atcctcccaa | ttgggacacg | cagtgttgag | acagacaagg | gaccctgga | 8520 |
| caaagaggcc | atagaagaaa | gggttgagag | gataaaatct | gagtacatga | cctcttggtt | 8580 |
| ttatgacaat | gacaacccct | acaggacctg | gcactactgt | ggctcctatg | tcacaaaaac | 8640 |
| ctcaggaagt | gcggcgagca | tggtaaatgg | tgttattaaa | attctgacat | atccatggga | 8700 |
| caggatagag | gaggtcacaa | gaatggcaat | gactgacaca | accccttttg | gacagcaaag | 8760 |
| agtgtttaaa | gaaaagttg | acaccagagc | aaaggatcca | ccagcgggaa | ctaggaagat | 8820 |
| catgaaagtt | gtcaacaggt | ggctgttccg | ccacctggcc | agagaaaaga | ccccagact | 8880 |
| gtgcacaaag | gaagaattta | ttgcaaaagt | ccgaagtcat | gcagccattg | agcttacct | 8940 |
| ggaagaacaa | gaacagtgga | agactgccaa | tgaggctgtc | caagacccaa | agttctggga | 9000 |
| actggtggat | gaagaaagga | agctgcacca | acaaggcagg | tgtcggactt | gtgtgtacaa | 9060 |
| catgatgggg | aaaagagaga | agaagctgtc | agagtttggg | aaagcaaagg | gaagccgtgc | 9120 |
| catatggtat | atgtggctgg | gagcgcggta | tcttgagttt | gaggccctgg | gattcctgaa | 9180 |
| tgaggaccat | tgggcttcca | gggaaaactc | aggaggagga | gtggaaggca | ttggcttaca | 9240 |
| atacctagga | tatgtgatca | gagacctggc | tgcaatggat | ggtggtggat | tctacgcgga | 9300 |
| tgacaccgct | ggatgggaca | cgcgcatcac | agaggcagac | cttgatgatg | aacaggagat | 9360 |
| cttgaactac | atgagcccac | atcacaaaaa | actggcacaa | gcagtgatgg | aaatgacata | 9420 |
| caagaacaaa | gtggtgaaag | tgttgagacc | agccccagga | gggaaagcct | acatggatgt | 9480 |
| cataagtcga | cgagaccaga | gaggatccgg | gcaggtagtg | acttatgctc | tgaacaccat | 9540 |
| caccaacttg | aaagtccaat | tgatcagaat | ggcagaagca | gagatggtga | tacatcacca | 9600 |
| acatgttcaa | gattgtgatg | aatcagttct | gaccaggctg | gaggcatggc | tcactgagca | 9660 |
| cggatgtgac | agactgaaga | ggatggcggt | gagtggagac | gactgtgtgg | tccggcccat | 9720 |
| cgatgacagg | ttcggcctgg | ccctgtccca | tctcaacgcc | atgtccaagg | ttagaaagga | 9780 |
| catatctgaa | tggcagccat | caaaaggggtg | gaatgattgg | gagaatgtgc | cttctgttc | 9840 |
| ccaccacttc | catgaactac | agctgaagga | tggcaggagg | attgtggtgc | cttgccgaga | 9900 |
| acaggacgag | ctcattggga | gaggaagggt | gtctccagga | aacggctgga | tgatcaagga | 9960 |

```
aacagcttgc ctcagcaaag cctatgccaa catgtggtca ctgatgtatt ttcacaaaag    10020
ggacatgagg ctactgtcat tggctgtttc ctcagctgtt cccacctcat gggttccaca    10080
aggacgcaca acatggtcga ttcatgggaa aggggagtgg atgaccacgg aagacatgct    10140
tgaggtgtgg aacagagtat ggataaccaa caacccacac atgcaggaca agacaatggt    10200
gaaaaaatgg agagatgtcc cttatctaac caagagacaa gacaagctgt gcggatcact    10260
gattggaatg accaataggg ccacctgggc ctcccacatc catttagtca tccatcgtat    10320
ccgaacgctg attggacagg agaaatacac tgactaccta acagtcatgg acaggtattc    10380
tgtggatgct gacctgcaac tgggtgagct tatctgaaac accatctaac aggaataacc    10440
gggatacaaa ccacgggtgg agaaccggac tccccacaac ctgaaaccgg gatataaacc    10500
acggctggag aaccgggctc cgcacttaaa atgaaacaga aaccgggata aaaactacgg    10560
atggagaacc ggactccaca cattgagaca gaagaagttg tcagcccaga accccacacg    10620
agttttgcca ctgctaagct gtgaggcagt gcaggctggg acagccgacc tccaggttgc    10680
gaaaaacctg gtttctggga cctcccaccc cagagtaaaa agaacggagc ctccgctacc    10740
accctcccac gtggtggtag aaagacgggg tctagaggtt agaggagacc ctccagggaa    10800
caaatagtgg gaccatattg acgccaggga agaccggagt tggttctctg cttttcctcc    10860
agaggtctgt gagcacagtt tgctcaagaa taagcagacc tttggatgac aaacacaaaa    10920
ccactgggtc ggcatggcat ctccacctcc tcgcggtccg acctgggcta cttcggtagg    10980
ctaagggaga aggcggccgc                                                11000
```

<210> SEQ ID NO 4
<211> LENGTH: 11000
<212> TYPE: DNA
<213> ORGANISM: Artificial
<220> FEATURE:
<223> OTHER INFORMATION: Synthetic construct

<400> SEQUENCE: 4

```
taatacgact cactatagag taaatcctgt gtgctaattg aggtgcattg gtctgcaaat      60
cgagttgcta ggcaataaac acatttggat taattttaat cgttcgttga gcgattagca     120
gagaactgac cagaacatgt ctggtcgtaa agctcaggga aaaccctggg cgtcaatat     180
ggtacgacga ggagttcgct ccttgtcaaa caaaataaaa caaaaaacaa acaaattgg     240
aaacagacct ggaccttcaa gaggtgttca aggatttatc tttttctttt tgttcaacat     300
tttgactgga aaaagatca cagcccacct aaagaggttg tggaaaatgc tggacccaag     360
acaaggcttg gctgttctaa ggaaagtcaa gagagtggtg gccagtttga tgagaggatt     420
gtcctcaagg aaacgccgtt cccatgatgt tctgactgtg caattcctaa tttttgggaat    480
gctgttgatg acgggtggag tgaccttggt gcggcgtggg agcgcttact atatgtactt     540
ggacagaaac gatgctgggg aggccatatc ttttccaacc acattgggga tgaataagtg     600
ttatatacag atcatggatc ttggacacat gtgtgatgcc accatgagct atgaatgccc     660
tatgctggat gagggggtgg aaccagatga cgtcgattgt tggtgcaaca cgacgtcaac     720
ttgggttgtg tacggaacct gccatcacaa aaaaggtgaa gcacggagat caagaagagc     780
tgtgacgctc ccctcccatt ccactaggaa gctgcaaacg cggtcgcaaa cctggttgga     840
atcaagagaa tacacaaagc acttgattag agtcgaaaat tggatattca ggaaccctgg     900
cttcgcgtta gcagcagctg ccatcgcttg gcttttggga agctcaacga gccaaaaagt     960
catatacttg gtcatgatac tgctgattgc cccggcatac agcatcaggt gcataggagt    1020
```

```
cagcaatagg gactttgtgg aaggtatgtc aggtgggact tgggttgatg ttgtcttgga    1080
acatggaggt tgtgtcaccg taatggcaca ggacaaaccg actgtcgaca tagagctggt    1140
tacaacaaca gtcagcaaca tggcggaggt aagatcctac tgctatgagg catcaatatc    1200
agacatggct tcggacagcc gctgcccaac acaaggtgaa gcctaccttg acaagcaatc    1260
agacactcaa tatgtctgca aaagaacgtt ggtggacaga ggctggggaa atggatgtgg    1320
attctttggc aaagggagcc tggtgacatg cgctaagttt gcatgctcca agaaaatgac    1380
cgggaagagc atccagccag agaatctgga gtacaagata atgctgtcag ttcatggctc    1440
ccagcacagt gggatgatcg ttaatgacac aggacatgaa actgatgaga atagagcgaa    1500
ggttgagata acgcccaatt caccaagagt tgaagccacc ctgggggggtt ttggaagcct    1560 aggacttgat tgtgaaccga ggacaggcct tgacttttca gatttgtatt acttgactat    1620
gaataacaag cattggttgg ttcacaagga gtggttccac gacattccat taccttggca    1680
cgctggggca gacaccggaa ctccacactg gaacaacaaa gaagcactgg tagagttcaa    1740
ggacgcacat gccaaaaggc aaactgtcgt ggttctaggg agtcaagaag gagcagttca    1800
ccacgccctt gctggagctc tggaggctga atggatggt gcaaagggaa tgctgtcctc    1860
tggccacttg aaatgtcgcc tgaaaatgga taaacttaga ttgaagggcg tgtcatactc    1920
cttgtgtacc gcagcgttca cattcaccaa gatcccggct gaaacactgc acgggacagt    1980
cacagtggag gtacagtacg caggggcaga tggaccctgc aaggttccag ctcagatggc    2040
ggtggacatg caaactctga ccccagttgg gaggttgata accgccaacc ccgtaatcac    2100
tgaaagcact gagaactcta agatgatgct ggaacttgat ccaccatttg ggactcttat    2160
cattgtcata ggagtcgggg agaagaagat caccccaccac tggcacagga gtggcagcac    2220
cattggaaaa gcatttgaag ccactgtgag aggtgccaag agaatggcag tcttgggaga    2280
cacagcctgg gactttggat cagttggagg cgctctcaac tcattgggca agggcatcca    2340
tcaaattttt ggagcagctt tcaaatcatt gtttggagga atgtcctggt tctcacaaat    2400
cctcattgga acgttgctga tgtggttggg tctgaacaca aagaatggat ctatttccct    2460
tatgtgcttg gccttagggg gagtgttgat cttcttatcc ctaggagttg gcgccgatca    2520
aggatgcgcc atcaactttg caagagaga gctcaagtgc ggagatggta tcttcatatt    2580
tagagactct gatgactggc tgaacaagta ctcatactat ccagaagatc ctgtgaagct    2640
tgcatcaata gtgaaagcct cttttgaaga agggaagtgt ggcctaaatt cagttgactc    2700
ccttgagcat gagatgtgga aagcagggc agatgagatc aatgccattt ttgaggaaaa    2760
cgaggtggac atttctgttg tcgtgcagga tccaaagaat gtttaccaga gaggaactca    2820 tccatttttcc agaattcggg atggtctgca gtatggttgg aagacttggg gtaagaacct    2880
tgtgttctcc ccagggagga agaatggaag cttcatcata gatggaaagt ccaggaaaga    2940
atgcccgttt tcaaaccggg tctggaattc tttccagata gaggagtttg ggacgggagt    3000
gttcaccaca cgcgtgtaca tggacgcagt ctttgaatac accatagact gcgatggatc    3060
tatcttgggt gcagcggtga acggaaaaaa gagtgcccat ggctctccaa cattttggat    3120
gggaagtcat gaagtaaatg gacatggat gatccacacc ttgaggcat tagattacaa    3180 ggagtgtgag tggccactga cacatacgat tggaacatca gttgaagaga gtgaaatgtt    3240
catgccgaga tcaatcggag gcccagttag ctctcacaat catatccctg gatacaaggt    3300
tcagacgaac ggaccttgga tgcaggtacc actagaagtg aagagagaag cttgcccagg    3360
```

```
gactagcgtg atcattgatg gcaactgtga tggacgggga aaatcaacca gatccaccac    3420
ggatagcggg aaagttattc ctgaatggtg ttgccgctcc tgcacaatgc cgcctgtgag    3480
cttccatggt agtgatgggt gttggtatcc catggaaatt aggccaagga aaacgcatga    3540
aagccatctg gtgcgctcct gggttacagc tggagaaata catgctgtcc cttttggttt    3600
ggtgagcatg atgatagcaa tggaagtggt cctaaggaaa agacagggac caaagcaaat    3660
gttggttgga ggagtagtgc tcttgggagc aatgctggtc gggcaagtaa ctctccttga    3720
tttgctgaaa ctcacagtgg ctgtgggatt gcatttccat gagatgaaca atggaggaga    3780
cgccatgtat atggcgttga ttgctgcctt ttcaatcaga ccagggctgc tcatcggctt    3840
tgggctcagg accctatgga gccctcggga acgccttgtg ctgaccctag gagcagccat    3900
ggtggagatt gccttgggtg gcgtgatggg cggcctgtgg aagtatctaa atgcagtttc    3960
tctctgcatc ctgacaataa atgctgttgc ttctaggaaa gcatcaaata ccatcttgcc    4020
cctcatggct ctgttgacac ctgtcactat ggctgaggtg agacttgccg caatgttctt    4080
ttgtgccgtg gttatcatag gggtccttca ccagaatttc aaggacacct ccatgcagaa    4140
gactatacct ctggtggccc tcacactcac atcttacctg gcttgacac aaccttttt    4200 gggcctgtgt gcatttctgg caacccgcat atttgggcga aggagtatcc cagtgaatga    4260
ggcactcgca gcagctggtc tagtgggagt gctggcagga ctggcttttc aggagatgga    4320
gaacttcctt ggtccgattg cagttggagg actcctgatg atgctggtta gcgtggctgg    4380
gagggtggat gggctagagc tcaagaagct tggtgaagtt catgggaag aggaggcgga    4440 gatcagcggg agttccgccc gctatgatgt ggcactcagt gaacaagggg agttcaagct    4500
gctttctgaa gagaaagtgc catgggacca ggttgtgatg acctcgctgg ccttggttgg    4560
ggctgccctc catccatttg ctcttctgct ggtccttgct gggtggctgt ttcatgtcag    4620
gggagctagg agaagtgggg atgtcttgtg ggatattccc actcctaaga tcatcgagga    4680
atgtgaacat ctggaggatg ggattttatgg catattccag tcaaccttct tgggggcctc    4740
ccagcgagga gtgggagtgg cacagggagg ggtgttccac acaatgtggc atgtcacaag    4800
aggagctttc cttgtcagga atggcaagaa gttgattcca tcttgggctt cagtaaagga    4860
agaccttgtc gcctatggtg gctcatggaa gttggaaggc agatgggatg agaggaaga    4920 ggtccagttg atcgcggctg ttccaggaaa gaacgtggtc aacgtccaga caaaccgag    4980 cttgttcaaa gtgaggaatg ggggagaaat cggggctgtc gctcttgact atccgagtgg    5040
cacttcagga tctcctattg ttaacaggaa cggagaggtg attgggctgt acggcaatgg    5100
catccttgtc ggtgacaact ccttcgtgtc cgccatatcc agactgagg tgaaggaaga    5160 aggaaaggag gagctccaag agatcccgac aatgctaaag aaaggaatga caactgtcct    5220
tgattttcat cctggagctg ggaagacaag acgtttcctc ccacagatct tggccgagtg    5280
cgcacggaga cgcttgcgca ctcttgtgtt ggccccacc agggttgttc tttctgaaat    5340
gaaggaggct tttcacggcc tggacgtgaa attccacaca caggcttttt ccgctcacgg    5400
cagcgggaga gaagtcattg atgccatgtg ccatgccacc ctaacttaca ggatgttgga    5460
accaactagg gttgttaact gggaagtgat cattatggat gaagcccatt tttggatcc    5520 agctagcata gccgctagag gttgggcagc gcacagagct agggcaaatg aaagtgcaac    5580
aatcttgatg acagccacac cgcctgggac tagtgatgaa tttccacatt caaatggtga    5640
aatagaagat gttcaaacgg acatacccag tgagccctgg aacacagggc atgactggat    5700
cctagctgac aaaaggccca cggcatggtt ccttccatcc atcagagctg caaatgtcat    5760
```

```
ggctgcctct ttgcgtaagg ctggaaagag tgtggtggtc ctgaacagga aaacctttga   5820
gagagaatac cccacgataa agcagaagaa acctgacttt atattggcca ctgacatagc   5880
tgaaatggga gccaaccttt gcgtggagcg agtgctggat tgcaggacgg cttttaagcc   5940
tgtgcttgtg gatgaaggga ggaaggtggc aataaaaggg ccacttcgta tctccgcatc   6000
ctctgctgct caaaggaggg ggcgcattgg gagaaatccc aacagagatg gagactcata   6060
ctactattct gagcctacaa gtgaaaataa tgcccaccac gtctgctggt tggaggcctc   6120
aatgctcttg gacaacatgg aggtgagggg tggaatggtc gccccactct atggcgttga   6180
aggaactaaa acaccagttt ccctggtga aatgagactg agggatgacc agaggaaagt   6240
cttcagagaa ctagtgagga attgtgacct gcccgtttgg ctttcgtggc aagtggccaa   6300
ggctggtttg aagacgaatg atcgtaagtg gtgttttgaa ggccctgagg aacatgagat   6360
cttgaatgac agcggtgaaa cagtgaagtg cagggctcct ggaggagcaa agaagcctct   6420
gcgcccaagg tggtgtgatg aaagggtgtc atctgaccag agtgcgctgt ctgaatttat   6480
taagtttgct gaaggtagga ggggagctgc tgaagtgcta gttgtgctga gtgaactccc   6540
tgatttcctg gctaaaaaag gtggagaggc aatggatacc atcagtgtgt tcctccactc   6600
tgaggaaggc tctagggctt accgcaatgc actatcaatg atgcctgagg caatgacaat   6660
agtcatgctg tttatactgg ctggactact gacatcggga atggtcatct ttttcatgtc   6720
tcccaaaggc atcagtagaa tgtctatggc gatgggcaca atggccggct gtggatatct   6780
catgttcctt ggaggcgtca aacccactca catctcctat gtcatgctca tattctttgt   6840
cctgatggtg gttgtgatcc ccgagccagg gcaacaaagg tccatccaag acaaccaagt   6900
ggcataccct attattggca tcctgacgct ggtttcagcg gtggcagcca acgagctagg   6960
catgctggag aaaaccaaag aggacctctt tgggaagaag aacttaattc catctagtgc   7020
ttcaccctgg agttggccgg atcttgacct gaagccagga gctgcctgga cagtgtacgt   7080
tggcattgtt acaatgctct ctccaatgtt gcaccactgg atcaaagtcg aatatggcaa   7140
cctgtctctg tctggaatag cccagtcagc ctcagtcctt tctttcatgg acaaggggat   7200
accattcatg aagatgaata tctcggtcat aatgctgctg gtcagtggct ggaattcaat   7260
aacagtgatg cctctgctct gtggcatagg gtgcgccatg ctccactggt ctctcatttt   7320
acctggaatc aaagcgcagc agtcaaagct tgcacagaga agggtgttcc atggcgttgc   7380
cgagaaccct gtggttgatg ggaatccaac agttgacatt gaggaagctc ctgaaatgcc   7440 tgcccttttat gagaagaaac tggctctata tctccttctt gctctcagcc tagcttctgt   7500
tgccatgtgc agaacgcccc tttcattggc tgaaggcatt gtcctagcat cagctgcctt   7560
agggccgctc atagagggaa acaccagcct tctttggaat ggacccatgg ctgtctccat   7620
gacaggagtc atgaggggga atcactatgc ttttgtggga gtcatgtaca atctatggaa   7680
gatgaaaact ggcgccggg ggagcgcgaa tggaaaaact ttgggtgaag tctggaagag   7740
ggaactgaat ctgttggaca gcgacagtt tgagttgtat aaaaggaccg acattgtgga   7800
ggtggatcgt gatacggcac gcaggcattt ggccgaaggg aagtggacac cggggtggc   7860 ggtctccagg gggaccgcaa agttaaggtg gttccatgag cgtggctatg tcaagctgga   7920
aggtagggtg attgacctgg ggtgtggccg cggaggctgg tgttactacg ctgctgcgca   7980
aaaggaagtg agtgggggtca aaggatttac tcttggaaga gacggccatg agaaacccat   8040
gaatgtgcaa agtctgggat ggaacatcat caccttcaag gacaaaactg atatccaccg   8100
```

-continued

```
cctagaacca gtgaaatgtg acacccttt gtgtgacatt ggagagtcat catcgtcatc    8160
ggtcacagag ggggaaagga ccgtgagagt tcttgatact gtagaaaaat ggctggcttg    8220
tggggttgac aacttctgtg tgaaggtgtt agctccatac atgccagatg ttctcgagaa    8280
actggaattc tccaaagga ggtttggcgg aacagtgatc aggaaccctc tctccaggaa    8340
ttccactcat gaaatgtact acgtgtctgg agcccgcagc aatgtcacat ttactgtgaa    8400
ccaaacatcc cgcctcctga tgaggagaat gaggcgtcca actggaaaag tgaccctgga    8460
ggctgacgtc atcctcccaa ttgggacacg cagtgttgag acagacaagg gaccctgga     8520
caaagaggcc atagaagaaa gggttgagag gataaaatct gagtacatga cctcttggtt    8580
ttatgacaat gacaaccct acaggacctg gcactactgt ggctcctatg tcacaaaaac     8640
ctcaggaagt gcggcgagca tggtaaatgg tgttattaaa attctgacat atccatggga    8700
caggatagag gaggtcacaa gaatggcaat gactgacaca ccccttttg gacagcaaag     8760
agtgttaaa gaaaaagttg acaccagagc aaaggatcca ccagcgggaa ctaggaagat     8820
catgaaagtt gtcaacaggt ggctgttccg ccacctggcc agagaaaaga ccccagact     8880
gtgcacaaag gaagaattta ttgcaaaagt ccgaagtcat gcagccattg gagcttacct    8940
ggaagaacaa aacagtggaa agactgccaa tgaggctgtc aagacccaa agttctggga    9000
actggtggat gaagaaagga agctgccacca acaaggcagg tgtcggactt gtgtgtacaa   9060
catgatgggg aaaagagaga agaagctgtc agagtttggg aaagcaaagg gaagccgtgc    9120
catatggtat atgtggctgg agcgcggta tcttgagtt gaggccctgg gattcctgaa     9180
tgaggaccat tgggcttcca gggaaaactc aggaggagga gtggaaggca ttggcttaca    9240
atacctagga tatgtgatca gagacctggc tgcaatggat ggtggtggat tctacgcgga    9300
tgacaccgct ggatgggaca cgcgcatcac agaggcagac cttgatgatg aacaggagat    9360
cttgaactac atgagcccac atcacaaaaa actggcacaa gcagtgatgg aaatgacata    9420
caagaacaaa gtggtgaaag tgttgagacc agccccagga gggaaagcct acatggatgt    9480
cataagtcga cgagaccaga gaggatccgg gcaggtagtg acttatgctc tgaacaccat    9540
caccaacttg aaagtccaat tgatcagaat ggcagaagca gagatggtga tacatcacca    9600
acatgttcaa gattgtgatg aatcagttct gaccaggctg gaggcatggc tcactgagca    9660
cggatgtgac agactgaaga ggatggcggt gagtggagac gactgtgtgg tccggcccat    9720
cgatgacagg ttcggcctgg ccctgtccca tctcaacgcc atgtccaagg ttagaaagga    9780
catatctgaa tggcagccat caaaagggtg gaatgattgg gagaatgtgc ccttctgttc    9840
ccaccacttc catgaactac agctgaagga tggcaggagg attgtggtgc cttgccgaga    9900
acaggacgag ctcattggga gaggaagggt gtctccagga aacggctgga tgatcaagga    9960
aacagcttgc ctcagcaaag cctatgccaa catgtggtca ctgatgtatt tcacaaaag    10020
ggacatgagg ctactgtcat ggctgttt ctcagctgtt cccacctcat gggttccaca    10080
aggacgcaca acatggtcga ttcatgggaa aggggagtgg atgaccacgg aagacatgct    10140
tgaggtgtgg aacagagtat ggataaccaa caacccacac atgcaggaca agacaatggt    10200
gaaaaatgg agagatgtcc cttatctaac caagagacaa gacaagctgt gcggatcact    10260
gattggaatg accaataggg ccacctgggc ctcccacatc catttagtca tccatcgtat    10320
ccgaacgctg attggacagg agaaatacac tgactaccta acagtcatgg acaggtattc    10380
tgtggatgct gacctgcaac tgggtgagct tatctgaaac accatctaac aggaataacc    10440
gggatacaaa ccacgggtgg agaaccggac tccccacaac ctgaaaccgg gatataaacc    10500
```

-continued

```
acggctggag aaccgggctc cgcacttaaa atgaaacaga aaccgggata aaaactacgg    10560
atggagaacc ggactccaca cattgagaca gaagaagttg tcagcccaga accccacacg    10620
agttttgcca ctgctaagct gtgaggcagt gcaggctggg acagccgacc tccaggttgc    10680
gaaaaacctg gtttctggga cctcccaccc cagagtaaaa agaacggagc ctccgctacc    10740
accctcccac gtggtggtag aaagacgggg tctagaggtt agaggagacc tccagggaa     10800 caaatagtgg gaccatattg acgccaggga agaccggag tggttctctg cttttcctcc     10860
agaggtctgt gagcacagtt tgctcaagaa taagcagacc tttggatgac aaacacaaaa    10920
ccactgggtc ggcatggcat ctccacctcc tcgcggtccg acctgggcta cttcggtagg    10980
ctaagggaga aggcggccgc                                                11000
```

<210> SEQ ID NO 5
<211> LENGTH: 168
<212> TYPE: PRT
<213> ORGANISM: Artificial
<220> FEATURE:
<223> OTHER INFORMATION: Synthetic construct

<400> SEQUENCE: 5

```
Ala Glu Ile Thr Arg Arg Gly Ser Ala Tyr Tyr Met Tyr Leu Asp Arg
 1               5                   10                  15

Ser Asp Ala Gly Lys Ala Ile Ser Phe Ala Thr Thr Leu Gly Val Asn
            20                  25                  30

Lys Cys His Val Gln Ile Met Asp Leu Gly His Met Cys Asp Ala Thr
        35                  40                  45

Met Ser Tyr Glu Cys Pro Met Leu Asp Glu Gly Val Glu Pro Asp Asp
    50                  55                  60

Val Asp Cys Trp Cys Asn Thr Thr Ser Thr Trp Val Val Tyr Gly Thr
65                  70                  75                  80

Cys His His Lys Lys Gly Glu Ala Arg Arg Ser Arg Arg Ala Val Thr
                85                  90                  95

Leu Pro Ser His Ser Thr Arg Lys Leu Gln Thr Arg Ser Gln Thr Trp
            100                 105                 110

Leu Glu Ser Arg Glu Tyr Thr Lys His Leu Ile Lys Val Glu Asn Trp
        115                 120                 125

Ile Phe Arg Asn Pro Gly Phe Ala Leu Val Ala Val Ala Ile Ala Trp
    130                 135                 140

Leu Leu Gly Ser Ser Thr Ser Gln Lys Val Ile Tyr Leu Val Met Ile
145                 150                 155                 160

Leu Leu Ile Ala Pro Ala Tyr Ser
                165
```

<210> SEQ ID NO 6
<211> LENGTH: 75
<212> TYPE: PRT
<213> ORGANISM: Artificial
<220> FEATURE:
<223> OTHER INFORMATION: Synthetic construct

<400> SEQUENCE: 6

```
Ala Val Thr Leu Pro Ser His Ser Thr Arg Lys Leu Gln Thr Arg Ser
 1               5                   10                  15

Gln Thr Trp Leu Glu Ser Arg Glu Tyr Thr Lys His Leu Ile Lys Val
            20                  25                  30

Glu Asn Trp Ile Phe Arg Asn Pro Gly Phe Ala Leu Val Ala Val Ala
```

```
                    35                  40                  45
Ile Ala Trp Leu Leu Gly Ser Ser Thr Ser Gln Lys Val Ile Tyr Leu
 50                  55                  60

Val Met Ile Leu Leu Ile Ala Pro Ala Tyr Ser
 65                  70                  75

<210> SEQ ID NO 7
<211> LENGTH: 500
<212> TYPE: PRT
<213> ORGANISM: Artificial
<220> FEATURE:
<223> OTHER INFORMATION: Synthetic construct

<400> SEQUENCE: 7

Ile Arg Cys Ile Gly Val Ser Asn Arg Asp Phe Val Glu Gly Met Ser
 1               5                  10                  15

Gly Gly Thr Trp Val Asp Val Leu Glu His Gly Gly Cys Val Thr
                20                  25                  30

Val Met Ala Gln Asp Lys Pro Thr Val Asp Ile Glu Leu Val Thr Thr
             35                  40                  45

Thr Val Ser Asn Met Ala Glu Val Arg Ser Tyr Cys Tyr Glu Ala Ser
 50                  55                  60

Ile Ser Asp Met Ala Ser Asp Ser Arg Cys Pro Thr Gln Gly Glu Ala
 65                  70                  75                  80

Tyr Leu Asp Lys Gln Ser Asp Thr Gln Tyr Val Cys Lys Arg Thr Leu
                 85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190

Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
            260                 265                 270

Met Asp Gly Ala Lys Gly Arg Leu Phe Ser Gly His Leu Lys Cys Arg
        275                 280                 285

Leu Lys Met Asp Lys Leu Arg Leu Lys Gly Val Ser Tyr Ser Leu Cys
    290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
```

```
                    325                 330                 335

Ile Pro Val Gln Met Ala Val Asp Met Gln Thr Leu Thr Pro Val Gly
            340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500

<210> SEQ ID NO 8
<211> LENGTH: 6
<212> TYPE: PRT
<213> ORGANISM: Artificial
<220> FEATURE:
<223> OTHER INFORMATION: Synthetic construct

<400> SEQUENCE: 8

Gly Gly Gly Gly Gly Gly
1               5

<210> SEQ ID NO 9
<211> LENGTH: 6
<212> TYPE: PRT
<213> ORGANISM: Artificial
<220> FEATURE:
<223> OTHER INFORMATION: Synthetic construct

<400> SEQUENCE: 9

Gly Gly Gly Gly Gly Thr
1               5

<210> SEQ ID NO 10
<211> LENGTH: 6
<212> TYPE: PRT
<213> ORGANISM: Artificial
<220> FEATURE:
<223> OTHER INFORMATION: Synthetic construct

<400> SEQUENCE: 10

Gly Gly Gly Pro Pro Pro
1               5

<210> SEQ ID NO 11
<211> LENGTH: 7
<212> TYPE: PRT
<213> ORGANISM: Artificial
```

```
<220> FEATURE:
<223> OTHER INFORMATION: Synthetic construct

<400> SEQUENCE: 11

Gly Gly Gly Ala Pro Pro Pro
1               5

<210> SEQ ID NO 12
<211> LENGTH: 295
<212> TYPE: PRT
<213> ORGANISM: Artificial
<220> FEATURE:
<223> OTHER INFORMATION: Synthetic construct

<400> SEQUENCE: 12

Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
                20                  25                  30

Val Met Ala Gln Asp Lys Pro Thr Val Asp Ile Glu Leu Val Thr Thr
            35                  40                  45

Thr Val Ser Asn Met Ala Glu Val Arg Ser Tyr Cys Tyr Glu Ala Ser
        50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Phe Gly Lys Gly Ser Leu
            100                 105                 110

Val Thr Cys Ala Lys Phe Ala Cys Ser Lys Lys Met Thr Gly Lys Ser
        115                 120                 125

Ile Gln Pro Glu Asn Leu Glu Tyr Ile Met Leu Ser Val His Gly Ser
130                 135                 140

Gln His Ser Gly Met Ile Val Asn Asp Thr Gly His Glu Thr Asp Glu
145                 150                 155                 160

Asn Arg Ala Lys Val Glu Ile Thr Pro Asn Ser Pro Arg Glu Ala Thr
                165                 170                 175

Leu Gly Gly Phe Gly Ser Leu Gly Leu Asp Cys Glu Pro Arg Thr Gly
            180                 185                 190

Leu Asp Phe Ser Asp Leu Tyr Tyr Leu Thr Met Asn Asn Lys His Trp
        195                 200                 205

Leu Val His Lys Glu Trp Phe His Asp Ile Pro Leu Pro Trp His Ala
210                 215                 220

Gly Ala Asp Thr Gly Thr Pro His Trp Asn Asn Lys Glu Ala Leu Val
225                 230                 235                 240

Glu Phe Lys Asp Ala His Ala Lys Arg Gln Thr Val Val Val Leu Gly
                245                 250                 255

Ser Gln Glu Gly Ala Val His Ala Leu Ala Gly Ala Leu Glu Ala Glu
            260                 265                 270

Met Asp Gly Ala Lys Gly Leu Ser Ser Gly His Leu Lys Cys Arg Leu
        275                 280                 285

Lys Met Asp Lys Leu Arg Leu
290                 295
```

CHIMERIC VIRUSES ENCODING MUTANT ZIKA VIRUS ENVELOPE GLYCOPROTEINS

CROSS-REFERENCE TO RELATED APPLICATIONS

This application is the National Stage of International Application No. PCT/US2018/064201 filed Dec. 6, 2018, which claims the benefit of U.S. Provisional Application No. 62/595,510 filed Dec. 6, 2017. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 16129US_ST25.txt. The text file is 44 KB, was created on Mar. 22, 2022, and is being submitted electronically via EFS-Web.

BACKGROUND

Zika virus belongs to the flavivirus family of viruses, which include West Nile, Japanese encephalitis, yellow fever, dengue, and tick-borne encephalitis viruses. Zika can be passed from a pregnant woman to her fetus. Infection during pregnancy is believed to be the cause certain birth defects, including microcephaly. Furthermore, individuals infected by the Zika virus are at a higher risk of developing Guillain-Barré syndrome. There have been outbreaks of the Zika virus in the United States, Africa, Southeast Asia, Pacific Islands, parts of the Caribbean, and Central and South America. Thus, there is a need to develop a vaccine to prevent Zika infections.

Flaviviruses are icosahedral and contain a ribonucleic acid (RNA) genome encoding a single polypeptide. During maturation, this polypeptide is cleaved by proteases into structural proteins: anchored capsid (anC), precursor-membrane (prM), and glycoprotein (E). The precursor-membrane protein is cleaved providing the M protein for virion assembly (Zhang et al, EMBO J 22(11):2604-2613, 2003).

Vaccines exist for several related viruses in the flavivirus family, such as dengue, yellow fever, and Japanese encephalitis virus (Cohen, Science 351(6273):543-544, 2016). Arroyo et al. report the molecular basis for attenuation of neurovirulence of a yellow fever Virus/Japanese encephalitis virus chimera vaccine (ChimeriVax-JE). J Virol. 2001, 75(2):934-42. U.S. Pat. No. 6,696,281 reports chimeric flavivirus vaccines containing a yellow fever virus. See also WO 2010085358, WO2014016360, and U.S. Patent Application Publication Number 2017/0014502.

References cited herein are not an admission of prior art.

SUMMARY

The present disclosure relates to Zika vaccines. In certain embodiments, this disclosure relates to vaccine compositions for use in methods of protecting a human subject against Zika disease or infection, wherein said composition comprises a vaccinal for Zika such as a live attenuated or inactivated chimeric Zika virus; live attenuated Zika virus; an inactivated Zika virus; a replication-defective pseudo-infectious Zika virus; a Zika virus-like particle (VLP), a Zika protein or combinations thereof. In certain embodiments, the Zika vaccinal comprises or encodes altered polypeptide sequenes disclosed herein.

In certain embodiments, the vaccine is a recombinant Yellow Fever virus encoding Zika virus protein(s). In certain embodiments, genes encoding the structural components of the Zika virus, including prM and E, are inserted into the backbone nucleic acid sequence of Yellow Fever virus, generating a chimeric virus. Typically, mutations in the prM, M, and/or E genes are made to reduce the neurotropism of the virus. In certain embodiments, the chimeric viruses as disclosed herein comprise a nucleic acid sequence encoding the Zika E protein comprising SEQ ID NO: 2 or a variant thereof. In certain embodiments, the variant has one, two, three, four, five, or more amino acid substitutions or conserved amino acid substitutions. In certain embodiments, the variant has SEQ ID NO: 1.

In certain embodiments, the variant comprises one, two, three, four, or all of the following substitutions relative to SEQ ID NO: 2: a) a phenylalanine (F) substitution at position 107; b) a lysine (K) substitution at position 138; c) a valine (V) substitution at position 176; d) a histidine (H) substitution at position 267; and/or e) a methionine (M) substitution at position 283.

In certain embodiments, the chimeric virus comprises a nucleic acid sequence having SEQ ID NO: 3 or SEQ ID NO: 4 or variant comprising synonymouns substitutions. In other embodiments, the disclosure relates to chimeric viruses comprising a nucleic acid having greater than 60%, 70%, 80%, 90%, or 95% sequence identity to SEQ ID NO: 3 or SEQ ID NO: 4 or variant having synonoymous substitutions. In other embodiments, the disclosure relates to the Zika virus, wherein the virus is attenuated by codon deoptimization.

In certain embodiments, this disclosure relates to non-naturally occurring Zika E proteins. In certain embodiments, this disclosure relates to non-naturally occurring virus particles or virus-like particles comprising a Zika E protein disclosed herein In certain embodiments, the Zika E protein comprises one, two, three, four, or all of the following substitutions relative to SEQ ID NO: 2: a) a phenylalanine (F) substitution at position 107; b) a lysine (K) substitution at position 138; c) a valine (V) substitution at position 176; d) a histidine (H) substitution at position 267; and/or e) a methionine (M) substitution at position 283.

In certain embodiments, this disclosure relates to recombinant nucleic acids and vectors comprising recombinant viral or chimeric viral geneomes or nucleic acids encoding proteins or polypeptides disclosed herein. In certain embodiments, this disclosure relates to cells or expression systems comprising said recombinant nucleic acids or vectors.

In certain embodiments, the disclosure relates to the use of a vaccine composition of the present disclosure for the manufacture of a medicament for protecting or treating a human subject against Zika disease or infection. In certain embodiments, the disclosure relates to treating a subject diagnosed with a Zika infection by administering a Zika composition disclosed herein in combination with another active agent or antiviral agent. In certain embodiments, a subject is a person who is diagnosed with exhibitiny sypmtoms or at risk of a Zika infection.

In certain embodiment, this disclosure relates to pharmaceutical compositions comprising a Zika composition disclosed herein and a pharmaceutically acceptable excipient. In certain embodiments, this disclosure relates to pharmaceutical compositions comprising Zika E proteins disclosed herein or a non-naturally occurring virus particle or virus-like particle comprising the same and a pharmaceutically acceptable excipient.

In certain embodiment, this disclosure relates to vaccines comprising a chimeric virus disclosed herein and an adjuvant. In certain embodiments, this disclosure relates to vaccine compositions comprising or encoding Zika E proteins disclosed herein or a non-naturally occurring virus particle or virus-like particle comprising the same and an adjuvant.

In certain embodiments, the disclosure relates to kits comprising a composition disclosed herein and instructions for the use of said composition in a method of treating or protecting a human subject against Zika disease or infection.

BRIEF DESCRIPTION OF THE DRAWINGS

FIG. 1A illustrates a ZIKV-YFV attenuated vaccine construct.

FIG. 2 illustrates a sequence comparison (SEQ ID NO: 12) between the first 300 amino acids of Zika E proteins. The query (Q or SEQ ID NO: 1) is a mutated sequence. The subject (S as SEQ ID NO: 2) is a wild-type sequence. The mutated sequence (SEQ ID NO: 1) contains a phenylalanine (F) substitution at position 107, a lysine (K) substitution at position 138, a valine (V) substitution at position 176, and a histidine (H) substitution at position 267. Also contemplated is a R283M mutation.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the term "combination with" when used to describe administration with an additional treatment means that the agent may be administered prior to, together with, or after the additional treatment, or a combination thereof.

As used herein, the terms "treat" and "treating" are not limited to the case where the subject (e.g., patient) is cured and the condition or disease is eradicated. Rather, embodiments, of the present disclosure also contemplate treatment that merely reduces symptoms, and/or delays conditions or disease progression. As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the term "nucleic acid" is intended to mean a ribonucleic or deoxyribonucleic acid or analog thereof, including a nucleic acid analyte presented in any context; for example, a probe, target or primer. A nucleic acid can include native or non-native bases. In this regard, a native deoxyribonucleic acid can have one or more bases selected from the group consisting of adenine, thymine, cytosine or guanine and a ribonucleic acid can have one or more bases selected from the group consisting of uracil, adenine, cytosine or guanine. It will be understood that a deoxyribonucleic acid used in the methods or compositions set forth herein can include uracil bases and a ribonucleic acid can include a thymine base.

The term "inactivated virus", as used herein, refers to a virus that has been rendered incapable of replication to any significant degree in host cells which would otherwise permit replication of the wild type virus. Inactivation may be achieved through several methods, including formalin or heat exposure.

The term "live attenuated virus", as used herein, refers to a virus whose virulence has been reduced by mutation, of at least one nucleotide, or by codon deoptimization (alteration of synonymous codons) or the deletion, or addition of a codon pair, while still keeping the virus viable such that the entire nucleotide sequence of the virus is not naturally occurring. It is understood that the terms provide for a modified virus having at least one mutation (i.e., a change in the nucleotide sequence) of at least one gene or non-coding sequence, which reduces its virulence as compared to naturally occurring virus. A live attenuated virus is contrasted with an inactivated virus.

The term "chimeric virus", as used herein, refers to a hybrid virus created by joining nucleic acid fragments from two or more different viruses or virus strain, in which the final virus contains essential genes necessary for replication; however, the entire nucleic acid sequence is not found in nature.

The term "Zika virus", as used herein, refers to the virus of the family Flaviviridae causing Zeka fever or Zika virus disease. Zika virus disease is often asymptomatic or with only mild symptoms. Zika virus infection increase the risk of developing the peripheral nerve disorder, Guillain-Barré syndrome. Similar to other Flaviviruses, Zika virus is icosahedral and contains a ribonucleic acid (RNA) genome of about 10.7 kB, encoding a single polypeptide. During maturation, this polypeptide is cleaved by proteases into structural and non-strutural proteins. Structural proteins include an anchored capsid (anC), precursor-membrane glycoprotein (prM), and glycoprotein (E). In the final step of virion assembly, prM is cleaved into an N-terminal precursor-peptide and an M protein (Zhang et al, EMBO J 22(11): 2604-2613, 2003).

Zika virus polyprotein is provides for in NCBI Reference Sequence: YP_002790881.1. The membrane glycoprotein precursor M has the following sequence:

(SEQ ID NO: 5)
AEITRRGSAYYMYLDRSDAGKAISFATTLGVNKCHVQIMDLGHMCDATMS

YECPMLDEGVEPDDVDCWCNTTSTWVVYGTCHHKKGEARRSRRAVTLPSH

STRKLQTRSQTWLESREYTKHLIKVENWIFRNPGFALVAVAIAWLLGSST

SQKVIYLVMILLIAPAYS.

Cleavage of the prM provides protein M with the sequence:

(SEQ ID NO: 6)
AVTLPSHSTRKLQTRSQTWLESREYTKHLIKVENWIFRNPGFALVAVAIA

WLLGSSTSQKVIYLVMILLIAPAYS.

Envelope protein E has the sequence:

(SEQ ID NO: 7)
IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIGYETDEDRAKVEVTPNSPRAEATLGGFGSLGLDCEPRTGLDFSDLYYL

TMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVS

YSLCTAAFTFTKVPAETLHGTVTVEVQYAGTDGPCKIPVQMAVDMQTLTP

VGRLITANPVITESTENSKMMLELDPPFGDSYIVIGVGDKKITHHWHRSG

STIGKAFEATVRGAKRMAVLGDTAWDFGSVGGVFNSLGKGIHQIFGAAFK

SLFGGMSWFSQILIGTLLVWLGLNTKNGSISLTCLALGGVMIFLSTAVS

A.

The term "virus-like particles or VLPs", as used herein, refers to virus particles that do not contain replicative genetic material but present at their surface a E protein in a repetitive ordered array similar to the virion structure. Typically, VLPs also contain prM and/or M, and E proteins. VLPs may be produced in vitro (Zhang et al, J. Virol. (2011) 30 (8):333). VLPs may also be produced in vivo. To that end, nucleic acid constructs (e.g. DNA or RNA constructs) encoding prM and E proteins may be introduced into a cell of a subject, e.g. a human subject, via methods known in the art, e.g. via use of a viral vector. Any viral vector may be used provided it is able to contain and express both prM and E Zika virus sequences.

The term "replication-defective pseudo-infectious virus", as used herein, refers to a virion particle that is replication-defective in vivo, owing to the absence in their genome of an essential sequence of the replicative cycle, for example the sequence encoding a capsid protein. However, the virion particles can propagate in a culture of helper cells that provide for the essential sequence(s) in trans. Replication-deficient pseudoinfectious viruses for use in the present disclosure include any virus according to the above definition which is capable of expressing the prM and E proteins of a Zika virus of any serotype or mutant disclosed herein. Examples include replication defective flavivirus/Zika chimeras such as replication defective YF/Zika, West Nile virus/Zika, and Japanese Encephalitis virus/Zika chimeras.

The term "$CCID_{50}$" refers to the quantity of virus (e.g. vaccinal virus) infecting 50% of the cell culture. The $CCID_{50}$ assay is a limit dilution assay with statistical titer calculation (Morrison D et al J Infect Dis. 2010; 201(3): 370-7)).

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG (SEQ ID NO: 8) and GGGGT (SEQ ID NO: 9) have a sequence identity of 4 out of 5 or 80%. For example, the polypeptides GGGPPP (SEQ ID NO: 10) and GGGAPPP (SEQ ID NO: 11) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q. The amino acid groups are also considered conserved substitutions.

The term "recombinant" when made in reference to a nucleic acid molecule refers to a nucleic acid molecule which is comprised of segments of nucleic acid joined together by means of molecular biological techniques. The term "recombinant" when made in reference to a protein or a polypeptide refers to a protein molecule which is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labeling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a recombinant vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-(3-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: $amp^r$, $cam^r$, $tet^r$, $blasticidin^r$, $neo^r$, $hyg^r$, $abx^r$, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (at1D), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB 1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "label receptor" refers to incorporation of a heterologous polypeptide in the receptor. A label includes the incorporation of a radiolabeled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to recombinant polypeptides comprising sequences disclosed herein or variants or fusions thereof wherein the amino terminal end or the carbon terminal end of the amino acid sequence are optionally attached to a heterologous amino acid sequence, label, or reporter molecule.

In certain embodiments, the disclosure relates to the recombinant vectors comprising a nucleic acid encoding a polypeptide disclosed herein or fusion protein thereof.

In certain embodiments, the recombinant vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the recombinant vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

Vaccines

In certain embodiments, this disclosure relates to vaccine compositions for use in methods of protecting a human subject against Zika disease or infection, wherein said composition comprises: a live attenuated or inactivated chimeric Zika virus; live attenuated Zika virus; an inactivated Zika virus; replication-defective pseudo-infectious Zida virus; a Zika virus-like particle (VLP) or combinations thereof. In certain embodiments, the chimeric or attenuated virus comprises mutations disclosed herein.

In certain embodiments, a vaccine of the instant disclosure is a recombinant Yellow Fever virus encoding Zika virus proteins. In certain embodiments, the vaccine has been attenuated or inactivated. In certain embodiments, genes encoding the structural components of the Zika virus, including prM, M, and E are inserted into the backbone nucleic acid sequence of Yellow Fever virus, generating a chimeric virus. Typically, mutations in the prM, M, and E genes are made to reduce the neurotropism of the virus.

In certain embodiments, this disclosure relates to an attenuated, live, chimeric virus comprising a yellow fever virus in which nucleotide sequences encoding structural components of the yellow fever virus are replaced with nucleotide sequences encoding structural components of a Zika virus. In other embodiments, this disclosure relates to chimeric viruses wherein the replaced nucleotide sequences encode for the precursor membrane protein (prM), membrane protein (M), and envelope (E) proteins of a Zika virus.

In certain embodiments, the disclosure contemplates a vaccinal Zika or uses disclosed herein that contains a polypeptide or a nucleic acid that encodes SEQ ID NO: 5, 6, and/or 7 or a polypeptide with 80, 90, 95, 96, 97, 98, or 99% or greater sequence identity or similarity thereto.

In certain embodiments, this disclosure relates to chimeric viruses wherein the nucleotide sequences of a Zika virus are derived from either the Asian or African strains or serotypes of Zika virus. In other embodiments, this disclosure relates to chimeric viruses wherein attenuation of the is accomplished through a series of mutations in the nucleotides encoding the precursor membrane protein, membrane protein, and envelope proteins are introduced, reducing the neurotropism of the virus.

In certain embodiments, the nucleic acid based vaccinal Zika as disclosed herein are capable of replication in a host cell or human subject. In certain embodiments, the nucleic acid based vaccinal Zika as disclosed herein are killed or inactivated, e.g., after replication that generates virus particles.

In certain embodiments, the chimeric viruses as disclosed herein comprises a nucleic acid sequence encoding the Zika E protein comprising SEQ ID NO: 2 or a variant thereof. In certain embodiments, the variant has one, two, three, or more amino acid substitutions or conserved amino acid substitutions. In certain embodiments, the variant has SEQ ID NO: 1.

In certain embodiments, the variant has the variant comprises one, two, three, four, or all of the following substitutions relative to SEQ ID NO: 2: a) a phenylalanine (F) substitution at position 107; b) a lysine (K) substitution at position 138; c) a valine (V) substitution at position 176; d) a histidine (H) substitution at position 267; and/or e) a methionine (M) substitution at position 283.

In certain embodiments, the chimeric virus comprises a nucleic acid sequence having SEQ ID NO: 3 or SEQ ID NO: 4 optionally comprising synonymouns substitutions. In other embodiments, the disclosure relates to chimeric viruses comprising a nucleic acid having greater than 60%, 70%, 80%, 90%, or 95% sequence identity to SEQ ID NO: 3 or SEQ ID NO: 4 or variant having synonymous substitutions. In other embodiments, the disclosure relates to the chimeric virus, wherein the virus is further attenuated by codon deoptimization.

The ability of a vaccine composition of the present disclosure to provoke an immune response in a subject (i.e. induce the production of neutralizing antibodies) can be assessed, for example, by measuring the neutralizing antibody titre raised against the Zika virus serotype(s) comprised within the composition. The neutralizing antibody titre may be measured by the Plaque Reduction Neutralization Test ($PRNT_{50}$) test. Briefly, neutralizing antibody titre is measured in sera collected from vaccinated subjects at least 28 days following administration of a vaccine composition of the present disclosure. Serial, two-fold dilutions of sera (previously heat-inactivated) are mixed with a constant challenge-dose of Zika virus as appropriate (expressed as PFU/mL). The mixtures are inoculated into wells of a microplate with confluent Vero cell monolayers. After adsorption, cell monolayers are incubated for a few days. The presence of Zika virus infected cells is indicated by the formation of infected foci and a reduction in virus infectivity due to the presence of neutralizing antibodies in the serum samples can thus be detected. The reported value (end point neutralization titre) represents the highest dilution of serum at which ≥50% of Zika challenge virus (in foci counts) is neutralized when compared to the mean viral focus count in the negative control wells (which represents the 100% virus load). The end point neutralization titres are presented as continuous values. As PRNT tests may slightly vary from a laboratory to another the LLOQ may also slightly vary. Accordingly, in a general manner, it is considered that seroconversion occurs when the titre is superior or equal to the LLOQ of the test.

A vaccine composition according to the present disclosure may be administered in a single dose. A vaccine composition according to the present disclosure may be administered in multiple doses. Doses of a vaccine composition according to the present disclosure may be administered in an initial vaccination regimen followed by booster vaccinations. For example, a vaccine composition according to the present disclosure may be administered in one, two or three doses or more than three doses, e.g. four doses. Preferably, the first dose and the third dose are to be administered approximately twelve months apart. For example, an initial vaccination regimen according to the present disclosure is administered in three doses, wherein the first and third doses of said vaccination regimen are to be administered approximately twelve months apart. Advantageously, a vaccine composition according to the present disclosure is to be administered in a first dose, a second dose and a third dose. In such an embodiment, said first dose and said third dose may be administered approximately twelve months apart. For instance, a vaccine composition of the present disclosure may be administered in a first dose, a second dose and a third dose, wherein said second dose is to be administered about six months after said first dose and wherein said third dose is to be administered about twelve months after said first dose. Alternatively, the three doses may be administered at zero months, at about three to four months (e.g. at about three-and-a-half months) and at about twelve months (i.e. a regimen wherein the second dose of the composition is administered at about three-and-a-half months after the first dose, and wherein the third dose of the composition is administered at about twelve months after the first dose).

A vaccine composition for use the present disclosure, e.g. for use in a method according to the present disclosure preferably comprises a Zika vaccinal. Such Zika vaccinal includes, for example, inactivated viruses, live attenuated viruses, and live attenuated chimeric Zika viruses. Preferably, the Zika vaccinal are live attenuated chimeric Zika viruses. Preferably, a live attenuated chimeric Zika virus according to the present disclosure comprises one or more proteins from a Zika virus and one or more proteins from a different flavivirus. Advantageously, said different flavivirus is a yellow fever virus, for example a yellow fever virus of strain YF 17D. Preferably, a chimeric Zika virus according to the present disclosure comprises the prM-E amino acid sequences of a Zika virus, for example, a chimeric Zika virus according to the present disclosure comprises a yellow fever virus genome whose prM-E whose prM-E sequence has been substituted with the prM-E sequence of a Zika virus.

The exact quantity of a Zika vaccinal of the present disclosure to be administered may vary according to the age and the weight of the patient being vaccinated, the frequency of administration as well as the other ingredients (e.g. adjuvants) in the composition. The quantity of a live attenuated Zika virus comprised in a vaccine composition of the present disclosure lies within a range of from about $10^3$ to about $10^7$ $CCID_{50}$. Generally, the quantity of a live attenuated Zika virus comprised in a vaccine composition of the present disclosure lies within a range of from about $10^3$ to about $10^6$ $CCID_{50}$ or of from about $10^3$ to about $10^7$ $CCID_{50}$, for example within a range of from about $5\times10^3$ to about $5\times10^5$ $CCID_{50}$, for example within a range of from about $1\times10^4$ to about $1\times10^5$ $CCID_{50}$, for example about $10^5$ $CCID_{50}$. The quantity of a live attenuated Zika virus comprised in a vaccine composition of the present disclosure may also lie within a range of from about $10^4$ to about $10^7$ $CCID_{50}$, for example about $10^6$ $CCID_{50}$. Generally, the quantity of a VLP comprised in the composition lies within a range of from about 100 ng to about 100 µg of VLP, preferably within a range of from about 100 ng to about 50 µg, preferably within a range of from about 100 ng to about 20 µg, preferably about 1 µg to 10 µg. The amount of VLP can be determined by ELISA. Advantageously, a vaccine composition according to the present disclosure comprises an effective amount of a Zika antigen as defined herein.

A vaccine composition for use in a method reported herein may optionally contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, human serum albumin, essential amino acids, nonessential amino acids, L-arginine hydrochlorate, saccharose, D-trehalose dehydrate, sorbitol, tris (hydroxymethyl) aminomethane and/or urea. In addition, the vaccine composition may optionally comprise pharmaceutically acceptable additives including, for example, diluents, binders, stabilizers, and preservatives.

A vaccine composition of the present disclosure may comprise a Zika antigen which is a Zika immunoprotein. A Zika immunoprotein, as used herein, is a Zika envelope (E) protein, or derivative or fragment thereof, that when administered to an immunocompetent subject induces neutralizing antibodies against a Zika virus. Zika immunoproteins include native and derivatized forms of Zika E proteins, including chemical conjugates, immunological fragments, and fusion proteins thereof.

Zika immunoproteins, or derivatives or fragments thereof may be conjugated to carrier molecules. Such conjugation may be achieved by chemical conjugation techniques or through the recombinant expression of fusion proteins comprising the Zika immunoproteins or derivatives or fragments thereof and the carrier molecule. Examples of carrier molecules which may be used for preparing conjugates include diphtheria toxoid, tetanus toxoid, fragment C of tetanus toxin, mutants of diphtheria toxin including CRM 197, CRM 176, CRM228, CRM 45, CRM 9, CRM 45, CRM 102, CRM 103 and CRM 107, pneumococcal pneumolysin, OMPC, heat shock proteins, pertussis proteins, pneumococcal surface protein PspA or the toxin A or B of *Clostridium difficile*.

In certain embodiments, the disclosure relates to a nucleic acid construct or viral vector which is able to express in a human cell a VLP comprising a Zika protein disclosed herein.

A vaccine composition of the present disclosure may comprise one or more adjuvants to enhance the immunogenicity of the Zika vaccinal. Those skilled in the art will be able to select an adjuvant which is appropriate in the context of this disclosure. An adjuvant is preferably used in a vaccine composition of the disclosure comprising an inactivated virus or a VLP or a Zika structural protein. An adjuvant may be used in a vaccine composition of the disclosure comprising a live attenuated virus, as long as said adjuvant does not influence replication.

Suitable adjuvants include an aluminum salt such as aluminum hydroxide gel, aluminum phosphate or alum, but may also be a salt of calcium, magnesium, iron or zinc. Further suitable adjuvants include an insoluble suspension of acylated tyrosine or acylated sugars, cationically or anionically derivatized saccharides, or polyphosphazenes. Alternatively, the adjuvant may be an oil-in-water emulsion adjuvant as well as combinations of oil-in-water emulsions and other active agents. Other oil emulsion adjuvants have been described, such as water-in-oil emulsions. Examples of such adjuvants include MF59, AF03 (WO 2007/006939), AF04 (WO 2007/080308), AF05, AF06 and derivatives thereof. The adjuvant may also be a saponin, lipid A or a derivative thereof, an immunostimulatory oligonucleotide, an alkyl glucosamide phosphate, an oil in water emulsion or combinations thereof. Examples of saponins include Quil A and purified fragments thereof such as QS7 and QS21.

As appreciated by skilled artisans, a vaccine composition of the present disclosure is suitably formulated to be compatible with the intended route of administration. Examples of suitable routes of administration include for instance intramuscular, transcutaneous, subcutaneous, intranasal, oral or intradermal. Advantageously, the route of administration is subcutaneous.

The vaccine compositions of the present disclosure may be administered using conventional hypodermic syringes or safety syringes or jet injectors. For intradermal administration, conventional hypodermic syringes may be employed using the Mantoux technique or specialized intradermal delivery devices and microinjection system.

The volume of a vaccine composition of the present disclosure administered will depend on the method of administration. In the case of subcutaneous injections, the volume is generally between 0.1 and 1.0 ml, preferably approximately 0.5 ml.

Optionally, booster administrations of a vaccine composition according to the present disclosure may be used, for example between six months and ten years, for example six months, one year, three years, five years or ten years after initial immunization (i.e. after administration of the last dose scheduled in the initial immunization regimen).

According to one embodiment, the disclosure also provides a kit comprising a vaccine composition of the disclosure and instructions for the use of said vaccine composition in a method of protecting a human subject against Zida disease. The kit can comprise at least one dose (typically in a syringe) of any vaccine composition contemplated herein. According to one embodiment the kit may comprises a multi-dose formulation (typically in a vial) of any vaccine composition as described herein. The kit further comprises a leaflet mentioning the use of the said vaccine composition for the prevention of Zika disease or the use of the said vaccine for the prophylaxis of Zika disease. The leaflet may further mention the vaccination regimen and the human subject population to be vaccinated.

Methods of Use

In certain embodiments, the disclosure relates to the use of a vaccine composition of the present disclosure for the manufacture of a medicament for protecting or treating a human subject against Zika disease or infection. In certain embodiments, a composition according to the present disclosure, e.g., a composition for use in a method according to the present disclosure reduces the incidence or likelihood of symptomatic virologically confirmed Zika infections.

In accordance with the present disclosure, a method of treating or protecting may results in a reduction in the severity or in the likelihood of developing Zika disease in a human subject exposed to a Zika virus. Advantageously, said reduction is statistically significant. For example, a method of protecting, according to the present disclosure, may result in a reduction in at least one symptom of Zika disease as defined herein or a reduction in a combination of any two or more of those symptoms. The protection may result in a statistically significant reduction in the incidence or likelihood of, e.g. the prevention of, symptomatic virologically-confirmed Zika disease caused by Zika virus of any serotype; a statistically significant reduction in the incidence or likelihood of, e.g. the prevention of Zika infection during pregnancy that can cause a birth defect, microcephaly or incomplete brain development caused by Zika virus of any serotype; a statistically significant reduction in the incidence or likelihood of, e.g. the prevention of fever, rash, headache, joint pain, conjunctivitis (red eyes), and/or muscle pain caused by Zika virus of any serotype; a statistically significant reduction in the incidence or likelihood of, e.g. the prevention of, fever or a reduction in the mean duration and/or intensity of fever; a statistically significant reduction in the incidence or likelihood of, e.g. the prevention of spreading the virus through mosquito bites and sex; and/or a statistically significant reduction in the incidence or likelihood of, e.g. the prevention passing Zika virus from a pregnant woman to her fetus. The duration and intensity of fever are monitored and recorded according to standard hospital procedures. In a human subject, a fever (i.e. a febrile episode) is defined as the observance of two temperature readings of at least 37.5° C. measured twice over an interval of at least 4 hours.

In certain embodiment, this disclosure relates to methods of vaccinating a subject against Zika virus comprising administering a Zika vaccinal as disclosed herein to a subject optionally in combination with an adjuvant under conditions such that antibodies that bind a Zika protein are generated in response to the vaccine. In certain embodiments, the antibodies are IgG antibodies in serum, or IgG or IgA antibodies in mucosal secretions or surfaces. In certain embodiments, one detects the presence of a given marker such as an antibody titer or a number of antigen-specific cells above a given threshold, e.g., an amount associated with a normal person in the absence of the vaccine.

In certain embodiment, this disclosure relates to methods of vaccinating a subject against Zika virus comprising administering a Zika vaccinal as disclosed herein to a subject optionally in combination with an adjuvant under conditions such that cells that produce antibodies that bind a Zika protein are generated in response to the vaccine.

In certain embodiments, the cells or antibodies are long live, e.g., cells or antibodies that detectably persist in the subject for longer than 6 months, 1 year, 2 years, 3 year, 5 years or more. In certain embodiments, the cells express CD3, CD4, and/or CD8. In certain embodiments, the cells are long-lived plasma cells secreting specific antibodies of adapted avidity and function, and isotype, even in the absence of virus. In certain embodiments, the cells are specific B and T memory cells of reactive memory or CD8+ cytotoxic T cells.

In certain embodiment, this disclosure relates to methods of treating or preventing a viral infection comprising administering a Zika vaccinal as disclosed herein to a subject optionally in combination with an adjuvant under conditions such that reduced titers of the Zika virus are generated after an infection. In certain embodiments, this disclosure relates to methods of treating or preventing a Zika viral infection comprising administering compositions disclosed herein to a subject optionally in combination with an adjuvant under conditions such that antibodies that bind a Zika protein are generated in response to the vaccine. In another embodiment, this disclosure relates to a method of vaccinating a patient against Zika virus infection by administering the above pharmaceutical composition along with a pharmaceutically acceptable adjuvant.

In certain embodiments, the disclosure relates to the use of a vaccine composition of the present disclosure for the manufacture of a medicament for protecting or treating a human subject against Zika disease or infection. In certain embodiments, the disclosure relates to treating a subject diagnosed with a Zika infection by administering a Zika antigen disclosed herein in combination with another active agent or antiviral agent. In certain embodiments, the agent is selected from a Zika neutralizing antibody, sofosbuvir, finasteride, ivermectin, brequinar, gemcitabine, epigallocatechin gallate, chloroquine, obatoclax, bortezomib, daptomycin, sertraline, pyrimethamine, cyclosporine A, azathioprine, emricasan, niclosamide, mefloquine, palonosetron, 25-hydroxycholesterol, 7-deaza-2'-C-methyladenosine (7-deaza-2"-CMA), 2"-C72, methyladenosine (2'-CMA), 2'-C-methylcytidine (2'-CMC), 2'-C-methylguanosine (2'-73 CMG), and 2'-C-methyluridine (2'-CMU).

A subject to which a vaccine composition of the disclosure is to be administered is preferably a person at risk of infection, for instance a person travelling in an area where Zika fever is present, i.e. a Zika endemic area, or a resident of such an area.

EXAMPLES

One can constructe YFV based live attenuated Zika virus (ZKV) vaccine, called "ZKV-YFV chimera vaccines" by introducing two types of genetic modifications into the 17D YFV genome. First, the prM, M and E genes of 17D YFV are replaced with the same genes of ZIKV, generating ZKV-YFV chimera viruses (FIG. 1). One can introduce a series of the prM/M/E gene mutations to reduce the neurotropism at the preM/M/E genes of the ZKV-YFV chimera virus in order to abolish potential neurotropism of ZKV, generating safe and effective YFV based live attenuated ZKV vaccines. A description of the vaccine gene constructs are shown in FIG. 1.

The sequence of YFV17D (NCBI: X03700) is publically available. One can produce "wild type" ZKV-YFV chimera virus by using ZKV strains (i.e. Rio-S1 strain: NCBI: KU926310).

One can synthesize chimera virus RNAs in vitro. One can transfect Vero cells to produce the live chimera viruses. Chimera viruses can be investigated for their replication kinetics compared with parental YFV17D and ZKV strains in Vero cells (i.e. MR766 and PR strain). One can determined neurotropism of both wild type and mutant chimera viruses by using various human neuronal cells and a newly tested mouse model as reported Lazear et al, Cell Host Microbe 19(5):720-730, 2016).

Nucleic acid sequences of wild type and mutant YF-ZK chimera viruses are attached, and examples of the E mutations to reduce viral neurotropism are marked in the mutant virus sequence.

```
YF-ZK Chimer with mutants (bold)
                                                    (SEQ ID NO: 4)
TAATACGACTCACTATAGAGTAAATCCTGTGTGCTAATTGAGGTGCATTGGTC

TGCAAATCGAGTTGCTAGGCAATAAACACATTTGGATTAATTTTAATCGTTCGTTGA

GCGATTAGCAGAGAACTGACCAGAACATGTCTGGTCGTAAAGCTCAGGGAAAAACC

CTGGGCGTCAATATGGTACGACGAGGAGTTCGCTCCTTGTCAAACAAAATAAAACA

AAAAACAAAACAAATTGGAAACAGACCTGGACCTTCAAGAGGTGTTCAAGGATTTA

TCTTTTTCTTTTTGTTCAACATTTTGACTGGAAAAAAGATCACAGCCCACCTAAAGAG

GTTGTGGAAAATGCTGGACCCAAGACAAGGCTTGGCTGTTCTAAGGAAAGTCAAGA

GAGTGGTGGCCAGTTTGATGAGAGGATTGTCCTCAAGGAAACGCCGTTCCCATGATG

TTCTGACTGTGCAATTCCTAATTTTGGGAATGCTGTTGATGACGGGTGGAGTGACCT

TGGTGCGGCGTGGGAGCGCTTACTATATGTACTTGGACAGAAACGATGCTGGGGAG

GCCATATCTTTTCCAACCACATTGGGGATGAATAAGTGTTATATACAGATCATGGAT

CTTGGACACATGTGTGATGCCACCATGAGCTATGAATGCCCTATGCTGGATGAGGGG

GTGGAACCAGATGACGTCGATTGTTGGTGCAACACGACGTCAACTTGGGTTGTGTAC

GGAACCTGCCATCACAAAAAAGGTGAAGCACGGAGATCAAGAAGAGCTGTGACGCT

CCCCTCCCATTCCACTAGGAAGCTGCAAACGCGGTCGCAAACCTGGTTGGAATCAA

GAGAATACACAAAGCACTTGATTAGAGTCGAAAATTGGATATTCAGGAACCCTGGC

TTCGCGTTAGCAGCAGCTGCCATCGCTTGGCTTTTGGGAAGCTCAACGAGCCAAAAA

GTCATATACTTGGTCATGATACTGCTGATTGCCCCGGCATACAGCATCAGGTGCATA

GGAGTCAGCAATAGGGACTTTGTGGAAGGTATGTCAGGTGGGACTTGGGTTGATGTT

GTCTTGGAACATGGAGGTTGTGTCACCGTAATGGCACAGGACAAACCGACTGTCGA

CATAGAGCTGGTTACAACAACAGTCAGCAACATGGCGGAGGTAAGATCCTACTGCT

ATGAGGCATCAATATCAGACATGGCTTCGGACAGCCGCTGCCCAACACAAGGTGAA

GCCTACCTTGACAAGCAATCAGACACTCAATATGTCTGCAAAAGAACGTTGGTGGA

CAGAGGCTGGGGAAATGGATGTGGATTCTTTGGCAAAGGGAGCCTGGTGACATGCG

CTAAGTTTGCATGCTCCAAGAAAATGACCGGGAAGAGCATCCAGCCAGAGAATCTG

GAGTACAAGATAATGCTGTCAGTTCATGGCTCCCAGCACAGTGGGATGATCGTTAAT

GACACAGGACATGAAACTGATGAGAATAGAGCGAAGGTTGAGATAACGCCCAATTC

ACCAAGAGTTGAAGCCACCCTGGGGGGTTTTGGAAGCCTAGGACTTGATTGTGAAC

CGAGGACAGGCCTTGACTTTTCAGATTTGTATTACTTGACTATGAATAACAAGCATT

GGTTGGTTCACAAGGAGTGGTTCCACGACATTCCATTACCTTGGCACGCTGGGGCAG

ACACCGGAACTCCACACTGGAACAACAAAGAAGCACTGGTAGAGTTCAAGGACGCA
```

-continued

CATGCCAAAAGGCAAACTGTCGTGGTTCTAGGGAGTCAAGAAGGAGCAGTTCACCA

CGCCCTTGCTGGAGCTCTGGAGGCTGAGATGGATGGTGCAAAGGAATGCTGTCCT

CTGGCCACTTGAAATGTCGCCTGAAAATGGATAAACTTAGATTGAAGGGCGTGTCAT

ACTCCTTGTGTACCGCAGCGTTCACATTCACCAAGATCCCGGCTGAAACACTGCACG

GGACAGTCACAGTGGAGGTACAGTACGCAGGGGCAGATGGACCCTGCAAGGTTCCA

GCTCAGATGGCGGTGGACATGCAAACTCTGACCCCAGTTGGGAGGTTGATAACCGC

CAACCCCGTAATCACTGAAAGCACTGAGAACTCTAAGATGATGCTGGAACTTGATCC

ACCATTTGGGGACTCTTACATTGTCATAGGAGTCGGGGAGAAGAAGATCACCCACC

ACTGGCACAGGAGTGGCAGCACCATTGGAAAAGCATTTGAAGCCACTGTGAGAGGT

GCCAAGAGAATGGCAGTCTTGGGAGACACAGCCTGGGACTTTGGATCAGTTGGAGG

CGCTCTCAACTCATTGGGCAAGGGCATCCATCAAATTTTTGGAGCAGCTTTCAAATC

ATTGTTTGGAGGAATGTCCTGGTTCTCACAAATCCTCATTGGAACGTTGCTGATGTG

GTTGGGTCTGAACACAAAGAATGGATCTATTTCCCTTATGTGCTTGGCCTTAGGGGG

AGTGTTGATCTTCTTATCCCTAGGAGTTGGCGCCGATCAAGGATGCGCCATCAACTT

TGGCAAGAGAGAGCTCAAGTGCGGAGATGGTATCTTCATATTTAGAGACTCTGATG

ACTGGCTGAACAAGTACTCATACTATCCAGAAGATCCTGTGAAGCTTGCATCAATAG

TGAAAGCCTCTTTTGAAGAAGGGAAGTGTGGCCTAAATTCAGTTGACTCCCTTGAGC

ATGAGATGTGGAGAAGCAGGGCAGATGAGATCAATGCCATTTTTGAGGAAAACGAG

GTGGACATTTCTGTTGTCGTGCAGGATCCAAAGAATGTTTACCAGAGAGGAACTCAT

CCATTTTCCAGAATTCGGGATGGTCTGCAGTATGGTTGGAAGACTTGGGGTAAGAAC

CTTGTGTTCTCCCCAGGGAGGAAGAATGGAAGCTTCATCATAGATGGAAAGTCCAG

GAAAGAATGCCCGTTTTCAAACCGGGTCTGGAATTCTTTCCAGATAGAGGAGTTTGG

GACGGGAGTGTTCACCACACGCGTGTACATGGACGCAGTCTTTGAATACACCATAG

ACTGCGATGGATCTATCTTGGGTGCAGCGGTGAACGGAAAAAAGAGTGCCCATGGC

TCTCCAACATTTTGGATGGGAAGTCATGAAGTAAATGGGACATGGATGATCCACACC

TTGGAGGCATTAGATTACAAGGAGTGTGAGTGGCCACTGACACATACGATTGGAAC

ATCAGTTGAAGAGAGTGAAATGTTCATGCCGAGATCAATCGGAGGCCCAGTTAGCT

CTCACAATCATATCCCTGGATACAAGGTTCAGACGAACGGACCTTGGATGCAGGTAC

CACTAGAAGTGAAGAGAGAAGCTTGCCCAGGGACTAGCGTGATCATTGATGGCAAC

TGTGATGGACGGGGAAAATCAACCAGATCCACCACGGATAGCGGGAAAGTTATTCC

TGAATGGTGTTGCCGCTCCTGCACAATGCCGCCTGTGAGCTTCCATGGTAGTGATGG

GTGTTGGTATCCCATGGAAATTAGGCCAAGGAAAACGCATGAAAGCCATCTGGTGC

GCTCCTGGGTTACAGCTGGAGAAATACATGCTGTCCCTTTTGGTTTGGTGAGCATGA

TGATAGCAATGGAAGTGGTCCTAAGGAAAAGACAGGGACCAAAGCAAATGTTGGTT

GGAGGAGTAGTGCTCTTGGGAGCAATGCTGGTCGGGCAAGTAACTCTCCTTGATTTG

CTGAAACTCACAGTGGCTGTGGGATTGCATTTCCATGAGATGAACAATGGAGGAGA

CGCCATGTATATGGCGTTGATTGCTGCCTTTTCAATCAGACCAGGGCTGCTCATCGG

CTTTGGGCTCAGGACCCTATGGAGCCCTCGGGAACGCCTTGTGCTGACCCTAGGAGC

AGCCATGGTGGAGATTGCCTTGGGTGGCGTGATGGGCGGCCTGTGGAAGTATCTAA

ATGCAGTTTCTCTCTGCATCCTGACAATAAATGCTGTTGCTTCTAGGAAAGCATCAA

ATACCATCTTGCCCCTCATGGCTCTGTTGACACCTGTCACTATGGCTGAGGTGAGAC

-continued

```
TTGCCGCAATGTTCTTTTGTGCCGTGGTTATCATAGGGGTCCTTCACCAGAATTTCAA

GGACACCTCCATGCAGAAGACTATACCTCTGGTGGCCCTCACACTCACATCTTACCT

GGGCTTGACACAACCTTTTTTGGGCCTGTGTGCATTTCTGGCAACCCGCATATTTGGG

CGAAGGAGTATCCCAGTGAATGAGGCACTCGCAGCAGCTGGTCTAGTGGGAGTGCT

GGCAGGACTGGCTTTTCAGGAGATGGAGAACTTCCTTGGTCCGATTGCAGTTGGAGG

ACTCCTGATGATGCTGGTTAGCGTGGCTGGGAGGGTGGATGGGCTAGAGCTCAAGA

AGCTTGGTGAAGTTTCATGGGAAGAGGAGGCGGAGATCAGCGGGAGTTCCGCCCGC

TATGATGTGGCACTCAGTGAACAAGGGGAGTTCAAGCTGCTTTCTGAAGAGAAAGT

GCCATGGGACCAGGTTGTGATGACCTCGCTGGCCTTGGTTGGGGCTGCCCTCCATCC

ATTTGCTCTTCTGCTGGTCCTTGCTGGGTGGCTGTTTCATGTCAGGGGAGCTAGGAG

AAGTGGGGATGTCTTGTGGGATATTCCCACTCCTAAGATCATCGAGGAATGTGAACA

TCTGGAGGATGGGATTTATGGCATATTCCAGTCAACCTTCTTGGGGGCCTCCCAGCG

AGGAGTGGGAGTGGCACAGGGAGGGGTGTTCCACACAATGTGGCATGTCACAAGAG

GAGCTTTCCTTGTCAGGAATGGCAAGAAGTTGATTCCATCTTGGGCTTCAGTAAAGG

AAGACCTTGTCGCCTATGGTGGCTCATGGAAGTTGGAAGGCAGATGGGATGGAGAG

GAAGAGGTCCAGTTGATCGCGGCTGTTCCAGGAAAGAACGTGGTCAACGTCCAGAC

AAAACCGAGCTTGTTCAAAGTGAGGAATGGGGAGAAATCGGGGCTGTCGCTCTTG

ACTATCCGAGTGGCACTTCAGGATCTCCTATTGTTAACAGGAACGGAGAGGTGATTG

GGCTGTACGGCAATGGCATCCTTGTCGGTGACAACTCCTTCGTGTCCGCCATATCCC

AGACTGAGGTGAAGGAAGAAGGAAAGGAGGAGCTCCAAGAGATCCCGACAATGCT

AAAGAAAGGAATGACAACTGTCCTTGATTTTCATCCTGGAGCTGGGAAGACAAGAC

GTTTCCTCCCACAGATCTTGGCCGAGTGCGCACGGAGACGCTTGCGCACTCTTGTGT

TGGCCCCCACCAGGGTTGTTCTTTCTGAAATGAAGGAGGCTTTTCACGGCCTGGACG

TGAAATTCCACACACAGGCTTTTTCCGCTCACGGCAGCGGGAGAGAAGTCATTGATG

CCATGTGCCATGCCACCCTAACTTACAGGATGTTGGAACCAACTAGGGTTGTTAACT

GGGAAGTGATCATTATGGATGAAGCCCATTTTTTGGATCCAGCTAGCATAGCCGCTA

GAGGTTGGGCAGCGCACAGAGCTAGGGCAAATGAAAGTGCAACAATCTTGATGACA

GCCACACCGCCTGGGACTAGTGATGAATTTCCACATTCAAATGGTGAAATAGAAGA

TGTTCAAACGGACATACCCAGTGAGCCCTGGAACACAGGGCATGACTGGATCCTAG

CTGACAAAAGGCCCACGGCATGGTTCCTTCCATCCATCAGAGCTGCAAATGTCATGG

CTGCCTCTTTGCGTAAGGCTGGAAAGAGTGTGGTGGTCCTGAACAGGAAAACCTTTG

AGAGAGAATACCCCACGATAAAGCAGAAGAAACCTGACTTTATATTGGCCACTGAC

ATAGCTGAAATGGGAGCCAACCTTTGCGTGGAGCGAGTGCTGGATTGCAGGACGGC

TTTTAAGCCTGTGCTTGTGGATGAAGGGAGGAAGGTGGCAATAAAAGGGCCACTTC

GTATCTCCGCATCCTCTGCTGCTCAAAGGAGGGGGCGCATTGGGAGAAATCCCAAC

AGAGATGGAGACTCATACTACTATTCTGAGCCTACAAGTGAAAATAATGCCCACCA

CGTCTGCTGGTTGGAGGCCTCAATGCTCTTGGACAACATGGAGGTGAGGGGTGGAA

TGGTCGCCCCACTCTATGGCGTTGAAGGAACTAAAACACCAGTTTCCCCTGGTGAAA

TGAGACTGAGGGATGACCAGAGGAAAGTCTTCAGAGAACTAGTGAGGAATTGTGAC

CTGCCCGTTTGGCTTTCGTGGCAAGTGGCCAAGGCTGGTTTGAAGACGAATGATCGT
```

-continued

```
AAGTGGTGTTTTGAAGGCCCTGAGGAACATGAGATCTTGAATGACAGCGGTGAAAC
AGTGAAGTGCAGGGCTCCTGGAGGAGCAAAGAAGCCTCTGCGCCCAAGGTGGTGTG
ATGAAAGGGTGTCATCTGACCAGAGTGCGCTGTCTGAATTTATTAAGTTTGCTGAAG
GTAGGAGGGGAGCTGCTGAAGTGCTAGTTGTGCTGAGTGAACTCCCTGATTTCCTGG
CTAAAAAAGGTGGAGAGGCAATGGATACCATCAGTGTGTTCCTCCACTCTGAGGAA
GGCTCTAGGGCTTACCGCAATGCACTATCAATGATGCCTGAGGCAATGACAATAGTC
ATGCTGTTTATACTGGCTGGACTACTGACATCGGGAATGGTCATCTTTTTCATGTCTC
CCAAAGGCATCAGTAGAATGTCTATGGCGATGGGCACAATGGCCGGCTGTGGATAT
CTCATGTTCCTTGGAGGCGTCAAACCCACTCACATCTCCTATGTCATGCTCATATTCT
TTGTCCTGATGGTGGTTGTGATCCCCGAGCCAGGGCAACAAAGGTCCATCCAAGACA
ACCAAGTGGCATACCTCATTATTGGCATCCTGACGCTGGTTTCAGCGGTGGCAGCCA
ACGAGCTAGGCATGCTGGAGAAAACCAAAGAGGACCTCTTTGGGAAGAAGAACTTA
ATTCCATCTAGTGCTTCACCCTGGAGTTGGCCGGATCTTGACCTGAAGCCAGGAGCT
GCCTGGACAGTGTACGTTGGCATTGTTACAATGCTCTCTCCAATGTTGCACCACTGG
ATCAAAGTCGAATATGGCAACCTGTCTCTGTCTGGAATAGCCCAGTCAGCCTCAGTC
CTTTCTTTCATGGACAAGGGGATACCATTCATGAAGATGAATATCTCGGTCATAATG
CTGCTGGTCAGTGGCTGGAATTCAATAACAGTGATGCCTCTGCTCTGTGGCATAGGG
TGCGCCATGCTCCACTGGTCTCTCATTTTACCTGGAATCAAAGCGCAGCAGTCAAAG
CTTGCACAGAGAAGGGTGTTCCATGGCGTTGCCGAGAACCCTGTGGTTGATGGGAAT
CCAACAGTTGACATTGAGGAAGCTCCTGAAATGCCTGCCCTTTATGAGAAGAAACTG
GCTCTATATCTCCTTCTTGCTCTCAGCCTAGCTTCTGTTGCCATGTGCAGAACGCCCT
TTTCATTGGCTGAAGGCATTGTCCTAGCATCAGCTGCCTTAGGGCCGCTCATAGAGG
GAAACACCAGCCTTCTTTGGAATGGACCCATGGCTGTCTCCATGACAGGAGTCATGA
GGGGAATCACTATGCTTTTGTGGGAGTCATGTACAATCTATGGAAGATGAAAACTG
GACGCCGGGGAGCGCGAATGGAAAAACTTTGGGTGAAGTCTGGAAGAGGGAACT
GAATCTGTTGGACAAGCGACAGTTTGAGTTGTATAAAAGGACCGACATTGTGGAGG
TGGATCGTGATACGGCACGCAGGCATTTGGCCGAAGGGAAGGTGGACACCGGGGTG
GCGGTCTCCAGGGGGACCGCAAAGTTAAGGTGGTTCCATGAGCGTGGCTATGTCAA
GCTGGAAGGTAGGGTGATTGACCTGGGGTGTGGCCGCGGAGGCTGGTGTTACTACG
CTGCTGCGCAAAAGGAAGTGAGTGGGGTCAAAGGATTTACTCTTGGAAGAGACGGC
CATGAGAAACCCATGAATGTGCAAAGTCTGGGATGGAACATCATCACCTTCAAGGA
CAAAACTGATATCCACCGCCTAGAACCAGTGAAATGTGACACCCTTTTGTGTGACAT
TGGAGAGTCATCATCGTCATCGGTCACAGAGGGGGAAAGGACCGTGAGAGTTCTTG
ATACTGTAGAAAAATGGCTGGCTTGTGGGGTTGACAACTTCTGTGTGAAGGTGTTAG
CTCCATACATGCCAGATGTTCTCGAGAAACTGGAATTGCTCCAAAGGAGGTTTGGCG
GAACAGTGATCAGGAACCCTCTCTCCAGGAATTCCACTCATGAAATGTACTACGTGT
CTGGAGCCCGCAGCAATGTCACATTTACTGTGAACCAAACATCCCGCCTCCTGATGA
GGAGAATGAGGCGTCCAACTGGAAAAGTGACCCTGGAGGCTGACGTCATCCTCCCA
ATTGGGACACGCAGTGTTGAGACAGACAAGGGACCCCTGGACAAAGAGGCCATAGA
AGAAAGGGTTGAGAGGATAAAATCTGAGTACATGACCTCTTGGTTTTATGACAATG
ACAACCCCTACAGGACCTGGCACTACTGTGGCTCCTATGTCACAAAAAACCTCAGGA
```

-continued

```
AGTGCGGCGAGCATGGTAAATGGTGTTATTAAAATTCTGACATATCCATGGGACAG
GATAGAGGAGGTCACAAGAATGGCAATGACTGACACAACCCCTTTTGGACAGCAAA
GAGTGTTTAAAGAAAAAGTTGACACCAGAGCAAAGGATCCACCAGCGGGAACTAGG
AAGATCATGAAAGTTGTCAACAGGTGGCTGTTCCGCCACCTGGCCAGAGAAAAGAA
CCCCAGACTGTGCACAAAGGAAGAATTTATTGCAAAAGTCCGAAGTCATGCAGCCA
TTGGAGCTTACCTGGAAGAACAAGAACAGTGGAAGACTGCCAATGAGGCTGTCCAA
GACCCAAAGTTCTGGGAACTGGTGGATGAAGAAAGGAAGCTGCACCAACAAGGCA
GGTGTCGGACTTGTGTGTACAACATGATGGGGAAAAGAGAGAAGAAGCTGTCAGAG
TTTGGGAAAGCAAAGGGAAGCCGTGCCATATGGTATATGTGGCTGGGAGCGCGGTA
TCTTGAGTTTGAGGCCCTGGGATTCCTGAATGAGGACCATTGGGCTTCCAGGGAAAA
CTCAGGAGGAGGAGTGGAAGGCATTGGCTTACAATACCTAGGATATGTGATCAGAG
ACCTGGCTGCAATGGATGGTGGTGGATTCTACGCGGATGACACCGCTGGATGGGAC
ACGCGCATCACAGAGGCAGACCTTGATGATGAACAGGAGATCTTGAACTACATGAG
CCCACATCACAAAAAACTGGCACAAGCAGTGATGGAAATGACATACAAGAACAAA
GTGGTGAAAGTGTTGAGACCAGCCCCAGGAGGGAAAGCCTACATGGATGTCATAAG
TCGACGAGACCAGAGAGGATCCGGGCAGGTAGTGACTTATGCTCTGAACACCATCA
CCAACTTGAAAGTCCAATTGATCAGAATGGCAGAAGCAGAGATGGTGATACATCAC
CAACATGTTCAAGATTGTGATGAATCAGTTCTGACCAGGCTGGAGGCATGGCTCACT
GAGCACGGATGTGACAGACTGAAGAGGATGGCGGTGAGTGGAGACGACTGTGTGGT
CCGGCCCATCGATGACAGGTTCGGCCTGGCCCTGTCCCATCTCAACGCCATGTCCAA
GGTTAGAAAGGACATATCTGAATGGCAGCCATCAAAAGGGTGGAATGATTGGGAGA
ATGTGCCCTTCTGTTCCCACCACTTCCATGAACTACAGCTGAAGGATGGCAGGAGGA
TTGTGGTGCCTTGCCGAGAACAGGACGAGCTCATTGGGAGAGGAAGGGTGTCTCCA
GGAAACGGCTGGATGATCAAGGAAACAGCTTGCCTCAGCAAAGCCTATGCCAACAT
GTGGTCACTGATGTATTTTCACAAAAGGGACATGAGGCTACTGTCATTGGCTGTTTC
CTCAGCTGTTCCCACCTCATGGGTTCCACAAGGACGCACAACATGGTCGATTCATGG
GAAAGGGGAGTGGATGACCACGGAAGACATGCTTGAGGTGTGGAACAGAGTATGG
ATAACCAACAACCCACACATGCAGGACAAGACAATGGTGAAAAAATGGAGAGATG
TCCCTTATCTAACCAAGAGACAAGACAAGCTGTGCGGATCACTGATTGGAATGACC
AATAGGGCCACCTGGGCCTCCCACATCCATTTAGTCATCCATCGTATCCGAACGCTG
ATTGGACAGGAGAAATACACTGACTACCTAACAGTCATGGACAGGTATTCTGTGGA
TGCTGACCTGCAACTGGGTGAGCTTATCTGAAACACCATCTAACAGGAATAACCGG
GATACAAACCACGGGTGGAGAACCGGACTCCCCACAACCTGAAACCGGGATATAAA
CCACGGCTGGAGAACCGGGCTCCGCACTTAAAATGAAACAGAAACCGGGATAAAA
ACTACGGATGGAGAACCGGACTCCACACATTGAGACAGAAGAAGTTGTCAGCCCAG
AACCCCACACGAGTTTTGCCACTGCTAAGCTGTGAGGCAGTGCAGGCTGGGACAGC
CGACCTCCAGGTTGCGAAAAACCTGGTTTCTGGGACCTCCCACCCCAGAGTAAAAA
GAACGGAGCCTCCGCTACCACCCTCCCACGTGGTGGTAGAAAGACGGGGTCTAGAG
GTTAGAGGAGACCCTCCAGGGAACAAATAGTGGGACCATATTGACGCCAGGGAAAG
ACCGGAGTGGTTCTCTGCTTTTCCTCCAGAGGTCTGTGAGCACAGTTTGCTCAAGAA
```

TAAGCAGACCTTTGGATGACAAACACAAAACCACTGGGTCGGCATGGCATCTCCAC
CTCCTCGCGGTCCGACCTGGGCTACTTCGGTAGGCTAAGGGAGAAGGCGGCCGC

YF-ZK Chimera (SEQ ID NO: 3)
TAATACGACTCACTATAGAGTAAATCCTGTGTGCTAATTGAGGTGCATTGGTC
TGCAAATCGAGTTGCTAGGCAATAAACACATTTGGATTAATTTTAATCGTTCGTTGA
GCGATTAGCAGAGAACTGACCAGAACATGTCTGGTCGTAAAGCTCAGGGAAAAACC
CTGGGCGTCAATATGGTACGACGAGGAGTTCGCTCCTTGTCAAACAAAATAAAACA
AAAACAAAACAAATTGGAAACAGACCTGGACCTTCAAGAGGTGTTCAAGGATTTA
TCTTTTTCTTTTTGTTCAACATTTTGACTGGAAAAAAGATCACAGCCCACCTAAAGAG
GTTGTGGAAAATGCTGGACCCAAGACAAGGCTTGGCTGTTCTAAGGAAAGTCAAGA
GAGTGGTGGCCAGTTTGATGAGAGGATTGTCCTCAAGGAAACGCCGTTCCCATGATG
TTCTGACTGTGCAATTCCTAATTTTGGGAATGCTGTTGATGACGGGTGGAGTGACCT
TGGTGCGGCGTGGGAGCGCTTACTATATGTACTTGGACAGAAACGATGCTGGGGAG
GCCATATCTTTTCCAACCACATTGGGGATGAATAAGTGTTATATACAGATCATGGAT
CTTGGACACATGTGTGATGCCACCATGAGCTATGAATGCCCTATGCTGGATGAGGGG
GTGGAACCAGATGACGTCGATTGTTGGTGCAACACGACGTCAACTTGGGTTGTGTAC
GGAACCTGCCATCACAAAAAAGGTGAAGCACGGAGATCAAGAAGAGCTGTGACGCT
CCCCTCCCATTCCACTAGGAAGCTGCAAACGCGGTCGCAAACCTGGTTGGAATCAA
GAGAATACACAAAGCACTTGATTAGAGTCGAAAATTGGATATTCAGGAACCCTGGC
TTCGCGTTAGCAGCAGCTGCCATCGCTTGGCTTTTGGGAAGCTCAACGAGCCAAAAA
GTCATATACTTGGTCATGATACTGCTGATTGCCCCGGCATACAGCATCAGGTGCATA
GGAGTCAGCAATAGGGACTTTGTGGAAGGTATGTCAGGTGGGACTTGGGTTGATGTT
GTCTTGGAACATGGAGGTTGTGTCACCGTAATGGCACAGGACAAACCGACTGTCGA
CATAGAGCTGGTTACAACAACAGTCAGCAACATGGCGGAGGTAAGATCCTACTGCT
ATGAGGCATCAATATCAGACATGGCTTCGGACAGCCGCTGCCCAACACAAGGTGAA
GCCTACCTTGACAAGCAATCAGACACTCAATATGTCTGCAAAAGAACGTTGGTGGA
CAGAGGCTGGGAAATGGATGTGGACTTTTTGGCAAAGGGAGCCTGGTGACATGCG
CTAAGTTTGCATGCTCCAAGAAAATGACCGGGAAGAGCATCCAGCCAGAGAATCTG
GAGTACCGGATAATGCTGTCAGTTCATGGCTCCCAGCACAGTGGGATGATCGTTAAT
GACACAGGACATGAAACTGATGAGAATAGAGCGAAGGTTGAGATAACGCCCAATTC
ACCAAGAGCCGAAGCCACCCTGGGGGGTTTTGGAAGCCTAGGACTTGATTGTGAAC
CGAGGACAGGCCTTGACTTTTCAGATTTGTATTACTTGACTATGAATAACAAGCATT
GGTTGGTTCACAAGGAGTGGTTCCACGACATTCCATTACCTTGGCACGCTGGGGCAG
ACACCGGAACTCCACACTGGAACAACAAAGAAGCACTGGTAGAGTTCAAGGACGCA
CATGCCAAAAGGCAAACTGTCGTGGTTCTAGGGAGTCAAGAAGGAGCAGTTCACAC
GGCCCTTGCTGGAGCTCTGGAGGCTGAGATGGATGGTGCAAAGGGAAGGCTGTCCT
CTGGCCACTTGAAATGTCGCCTGAAAATGGATAAACTTAGATTGAAGGGCGTGTCAT
ACTCCTTGTGTACCGCAGCGTTCACATTCACCAAGATCCCGGCTGAAACACTGCACG
GGACAGTCACAGTGGAGGTACAGTACGCAGGGGCAGATGGACCCTGCAAGGTTCCA
GCTCAGATGGCGGTGGACATGCAAACTCTGACCCCAGTTGGGAGGTTGATAACCGC
CAACCCCGTAATCACTGAAAGCACTGAGAACTCTAAGATGATGCTGGAACTTGATCC -continued

```
ACCATTTGGGGACTCTTACATTGTCATAGGAGTCGGGGAGAAGAAGATCACCCACC

ACTGGCACAGGAGTGGCAGCACCATTGGAAAAGCATTTGAAGCCACTGTGAGAGGT

GCCAAGAGAATGGCAGTCTTGGGAGACACAGCCTGGGACTTTGGATCAGTTGGAGG

CGCTCTCAACTCATTGGGCAAGGGCATCCATCAAATTTTTGGAGCAGCTTTCAAATC

ATTGTTTGGAGGAATGTCCTGGTTCTCACAAATCCTCATTGGAACGTTGCTGATGTG

GTTGGGTCTGAACACAAAGAATGGATCTATTTCCCTTATGTGCTTGGCCTTAGGGGG

AGTGTTGATCTTCTTATCCCTAGGAGTTGGCGCCGATCAAGGATGCGCCATCAACTT

TGGCAAGAGAGCTCAAGTGCGGAGATGGTATCTTCATATTTAGAGACTCTGATG

ACTGGCTGAACAAGTACTCATACTATCCAGAAGATCCTGTGAAGCTTGCATCAATAG

TGAAAGCCTCTTTTGAAGAAGGGAAGTGTGGCCTAAATTCAGTTGACTCCCTTGAGC

ATGAGATGTGGAGAAGCAGGGCAGATGAGATCAATGCCATTTTTGAGGAAAACGAG

GTGGACATTTCTGTTGTCGTGCAGGATCCAAAGAATGTTTACCAGAGAGGAACTCAT

CCATTTTCCAGAATTCGGGATGGTCTGCAGTATGGTTGGAAGACTTGGGGTAAGAAC

CTTGTGTTCTCCCCAGGGAGGAAGAATGGAAGCTTCATCATAGATGGAAAGTCCAG

GAAAGAATGCCCGTTTTCAAACCGGGTCTGGAATTCTTTCCAGATAGAGGAGTTTGG

GACGGGAGTGTTCACCACACGCGTGTACATGGACGCAGTCTTTGAATACACCATAG

ACTGCGATGGATCTATCTTGGGTGCAGCGGTGAACGGAAAAAAGAGTGCCCATGGC

TCTCCAACATTTTGGATGGGAAGTCATGAAGTAAATGGGACATGGATGATCCACACC

TTGGAGGCATTAGATTACAAGGAGTGTGAGTGGCCACTGACACATACGATTGGAAC

ATCAGTTGAAGAGAGTGAAATGTTCATGCCGAGATCAATCGGAGGCCCAGTTAGCT

CTCACAATCATATCCCTGGATACAAGGTTCAGACGAACGGACCTTGGATGCAGGTAC

CACTAGAAGTGAAGAGAGAAGCTTGCCCAGGGACTAGCGTGATCATTGATGGCAAC

TGTGATGGACGGGGAAAATCAACCAGATCCACCACGGATAGCGGGAAAGTTATTCC

TGAATGGTGTTGCCGCTCCTGCACAATGCCGCCTGTGAGCTTCCATGGTAGTGATGG

GTGTTGGTATCCCATGGAAATTAGGCCAAGGAAAACGCATGAAAGCCATCTGGTGC

GCTCCTGGGTTACAGCTGGAGAAATACATGCTGTCCCTTTTGGTTTGGTGAGCATGA

TGATAGCAATGGAAGTGGTCCTAAGGAAAAGACAGGGACCAAAGCAAATGTTGGTT

GGAGGAGTAGTGCTCTTGGGAGCAATGCTGGTCGGGCAAGTAACTCTCCTTGATTTG

CTGAAACTCACAGTGGCTGTGGGATTGCATTTCCATGAGATGAACAATGGAGGAGA

CGCCATGTATATGGCGTTGATTGCTGCCTTTTCAATCAGACCAGGGCTGCTCATCGG

CTTTGGGCTCAGGACCCTATGGAGCCCTCGGGAACGCCTTGTGCTGACCCTAGGAGC

AGCCATGGTGGAGATTGCCTTGGGTGGCGTGATGGGCGGCCTGTGGAAGTATCTAA

ATGCAGTTTCTCTCTGCATCCTGACAATAAATGCTGTTGCTTCTAGGAAAGCATCAA

ATACCATCTTGCCCCTCATGGCTCTGTTGACACCTGTCACTATGGCTGAGGTGAGAC

TTGCCGCAATGTTCTTTTGTGCCGTGGTTATCATAGGGGTCCTTCACCAGAATTTCAA

GGACACCTCCATGCAGAAGACTATACCTCTGGTGGCCCTCACACTCACATCTTACCT

GGGCTTGACACAACCTTTTTTGGGCCTGTGTGCATTTCTGGCAACCCGCATATTTGGG

CGAAGGAGTATCCCAGTGAATGAGGCACTCGCAGCAGCTGGTCTAGTGGGAGTGCT

GGCAGGACTGGCTTTTCAGGAGATGGAGAACTTCCTTGGTCCGATTGCAGTTGGAGG

ACTCCTGATGATGCTGGTTAGCGTGGCTGGGAGGGTGGATGGGCTAGAGCTCAAGA
```

-continued

```
AGCTTGGTGAAGTTTCATGGGAAGAGGAGGCGGAGATCAGCGGGAGTTCCGCCCGC
TATGATGTGGCACTCAGTGAACAAGGGGAGTTCAAGCTGCTTTCTGAAGAGAAAGT
GCCATGGGACCAGGTTGTGATGACCTCGCTGGCCTTGGTTGGGGCTGCCCTCCATCC
ATTTGCTCTTCTGCTGGTCCTTGCTGGGTGGCTGTTTCATGTCAGGGGAGCTAGGAG
AAGTGGGGATGTCTTGTGGGATATTCCCACTCCTAAGATCATCGAGGAATGTGAACA
TCTGGAGGATGGGATTTATGGCATATTCCAGTCAACCTTCTTGGGGGCCTCCCAGCG
AGGAGTGGGAGTGGCACAGGGAGGGGTGTTCCACACAATGTGGCATGTCACAAGAG
GAGCTTTCCTTGTCAGGAATGGCAAGAAGTTGATTCCATCTTGGGCTTCAGTAAAGG
AAGACCTTGTCGCCTATGGTGGCTCATGGAAGTTGGAAGGCAGATGGGATGGAGAG
GAAGAGGTCCAGTTGATCGCGGCTGTTCCAGGAAAGAACGTGGTCAACGTCCAGAC
AAAACCGAGCTTGTTCAAAGTGAGGAATGGGGGAGAAATCGGGGCTGTCGCTCTTG
ACTATCCGAGTGGCACTTCAGGATCTCCTATTGTTAACAGGAACGGAGAGGTGATTG
GGCTGTACGGCAATGGCATCCTTGTCGGTGACAACTCCTTCGTGTCCGCCATATCCC
AGACTGAGGTGAAGGAAGAAGGAAAGGAGGAGCTCCAAGAGATCCCGACAATGCT
AAAGAAAGGAATGACAACTGTCCTTGATTTTCATCCTGGAGCTGGGAAGACAAGAC
GTTTCCTCCCACAGATCTTGGCCGAGTGCGCACGGAGACGCTTGCGCACTCTTGTGT
TGGCCCCCACCAGGTTGTTCTTTCTGAAATGAAGGAGGCTTTTCACGGCCTGGACG
TGAAATTCCACACACAGGCTTTTTCCGCTCACGGCAGCGGGAGAGAAGTCATTGATG
CCATGTGCCATGCCACCCTAACTTACAGGATGTTGGAACCAACTAGGGTTGTTAACT
GGGAAGTGATCATTATGGATGAAGCCCATTTTTTGGATCCAGCTAGCATAGCCGCTA
GAGGTTGGGCAGCGCACAGAGCTAGGGCAAATGAAAGTGCAACAATCTTGATGACA
GCCACACCGCCTGGGACTAGTGATGAATTTCCACATTCAAATGGTGAAATAGAAGA
TGTTCAAACGGACATACCCAGTGAGCCCTGGAACACAGGGCATGACTGGATCCTAG
CTGACAAAAGGCCCACGGCATGGTTCCTTCCATCCATCAGAGCTGCAAATGTCATGG
CTGCCTCTTTGCGTAAGGCTGGAAAGAGTGTGGTGGTCCTGAACAGGAAAACCTTTG
AGAGAGAATACCCCACGATAAAGCAGAAGAAACCTGACTTTATATTGGCCACTGAC
ATAGCTGAAATGGGAGCCAACCTTTGCGTGGAGCGAGTGCTGGATTGCAGGACGGC
TTTTAAGCCTGTGCTTGTGGATGAAGGGAGGAAGGTGGCAATAAAAGGGCCACTTC
GTATCTCCGCATCCTCTGCTGCTCAAAGGAGGGGCGCATTGGGAGAAATCCCAAC
AGAGATGGAGACTCATACTACTATTCTGAGCCTACAAGTGAAAATAATGCCCACCA
CGTCTGCTGGTTGGAGGCCTCAATGCTCTTGGACAACATGGAGGTGAGGGGTGGAA
TGGTCGCCCCACTCTATGGCGTTGAAGGAACTAAAACACCAGTTTCCCCTGGTGAAA
TGAGACTGAGGGATGACCAGAGGAAAGTCTTCAGAGAACTAGTGAGGAATTGTGAC
CTGCCCGTTTGGCTTTCGTGGCAAGTGGCCAAGGCTGGTTTGAAGACGAATGATCGT
AAGTGGTGTTTTGAAGGCCCTGAGGAACATGAGATCTTGAATGACAGCGGTGAAAC
AGTGAAGTGCAGGGCTCCTGGAGGAGCAAAGAAGCCTCTGCGCCCAAGGTGGTGTG
ATGAAAGGGTGTCATCTGACCAGAGTGCGCTGTCTGAATTTATTAAGTTTGCTGAAG
GTAGGAGGGGAGCTGCTGAAGTGCTAGTTGTGCTGAGTGAACTCCCTGATTTCCTGG
CTAAAAAAGGTGGAGAGGCAATGGATACCATCAGTGTGTTCCTCCACTCTGAGGAA
GGCTCTAGGGCTTACCGCAATGCACTATCAATGATGCCTGAGGCAATGACAATAGTC
ATGCTGTTTATACTGGCTGGACTACTGACATCGGGAATGGTCATCTTTTTCATGTCTC
```

-continued

```
CCAAAGGCATCAGTAGAATGTCTATGGCGATGGGCACAATGGCCGGCTGTGGATAT
CTCATGTTCCTTGGAGGCGTCAAACCCACTCACATCTCCTATGTCATGCTCATATTCT
TTGTCCTGATGGTGGTTGTGATCCCCGAGCCAGGGCAACAAAGGTCCATCCAAGACA
ACCAAGTGGCATACCTCATTATTGGCATCCTGACGCTGGTTTCAGCGGTGGCAGCCA
ACGAGCTAGGCATGCTGGAGAAAACCAAAGAGGACCTCTTTGGGAAGAAGAACTTA
ATTCCATCTAGTGCTTCACCCTGGAGTTGGCCGGATCTTGACCTGAAGCCAGGAGCT
GCCTGGACAGTGTACGTTGGCATTGTTACAATGCTCTCTCCAATGTTGCACCACTGG
ATCAAAGTCGAATATGGCAACCTGTCTCTGTCTGGAATAGCCCAGTCAGCCTCAGTC
CTTTCTTTCATGGACAAGGGGATACCATTCATGAAGATGAATATCTCGGTCATAATG
CTGCTGGTCAGTGGCTGGAATTCAATAACAGTGATGCCTCTGCTCTGTGGCATAGGG
TGCGCCATGCTCCACTGGTCTCTCATTTTACCTGGAATCAAAGCGCAGCAGTCAAAG
CTTGCACAGAGAAGGGTGTTCCATGGCGTTGCCGAGAACCCTGTGGTTGATGGGAAT
CCAACAGTTGACATTGAGGAAGCTCCTGAAATGCCTGCCCTTTATGAGAAGAAACTG
GCTCTATATCTCCTTCTTGCTCTCAGCCTAGCTTCTGTTGCCATGTGCAGAACGCCCT
TTTCATTGGCTGAAGGCATTGTCCTAGCATCAGCTGCCTTAGGGCCGCTCATAGAGG
GAAACACCAGCCTTCTTTGGAATGGACCCATGGCTGTCTCCATGACAGGAGTCATGA
GGGGGAATCACTATGCTTTTGTGGGAGTCATGTACAATCTATGGAAGATGAAAACTG
GACGCCGGGGAGCGCGAATGGAAAAACTTTGGGTGAAGTCTGGAAGAGGGAACT
GAATCTGTTGGACAAGCGACAGTTTGAGTTGTATAAAAGGACCGACATTGTGGAGG
TGGATCGTGATACGGCACGCAGGCATTTGGCCGAAGGGAAGGTGGACACCGGGGTG
GCGGTCTCCAGGGGGACCGCAAAGTTAAGGTGGTTCCATGAGCGTGGCTATGTCAA
GCTGGAAGGTAGGGTGATTGACCTGGGGTGTGGCCGCGGAGGCTGGTGTTACTACG
CTGCTGCGCAAAAGGAAGTGAGTGGGGTCAAAGGATTTACTCTTGGAAGAGACGGC
CATGAGAAACCCATGAATGTGCAAAGTCTGGGATGGAACATCATCACCTTCAAGGA
CAAAACTGATATCCACCGCCTAGAACCAGTGAAATGTGACACCCTTTTGTGTGACAT
TGGAGAGTCATCATCGTCATCGGTCACAGAGGGGGAAAGGACCGTGAGAGTTCTTG
ATACTGTAGAAAAATGGCTGGCTTGTGGGGTTGACAACTTCTGTGTGAAGGTGTTAG
CTCCATACATGCCAGATGTTCTCGAGAAACTGGAATTGCTCCAAAGGAGGTTTGGCG
GAACAGTGATCAGGAACCCTCTCTCCAGGAATTCCACTCATGAAATGTACTACGTGT
CTGGAGCCCGCAGCAATGTCACATTTACTGTGAACCAAACATCCCGCCTCCTGATGA
GGGAGAATGAGGCGTCCAACTGGAAAAGTGACCCTGGAGGCTGACGTCATCCTCCCA
ATTGGGACACGCAGTGTTGAGACAGACAAGGGACCCCTGGACAAAGAGGCCATAGA
AGAAAGGGTTGAGAGGATAAAATCTGAGTACATGACCTCTTGGTTTTATGACAATG
ACAACCCCTACAGGACCTGGCACTACTGTGGCTCCTATGTCACAAAAACCTCAGGA
AGTGCGGCGAGCATGGTAAATGGTGTTATTAAAATTCTGACATATCCATGGGACAG
GATAGAGGAGGTCACAAGAATGGCAATGACTGACACAACCCCTTTTGGACAGCAAA
GAGTGTTTAAAGAAAAAGTTGACACCAGAGCAAAGGATCCACCAGCGGGAACTAGG
AAGATCATGAAAGTTGTCAACAGGTGGCTGTTCCGCCACCTGGCCAGAGAAAAGAA
CCCCAGACTGTGCACAAAGGAAGAATTTATTGCAAAAGTCCGAAGTCATGCAGCCA
TTGGAGCTTACCTGGAAGAACAAGAACAGTGGAAGACTGCCAATGAGGCTGTCCAA
```

-continued

```
GACCCAAAGTTCTGGGAACTGGTGGATGAAGAAAGGAAGCTGCACCAACAAGGCA

GGTGTCGGACTTGTGTGTACAACATGATGGGGAAAAGAGAGAAGAAGCTGTCAGAG

TTTGGGAAAGCAAAGGGAAGCCGTGCCATATGGTATATGTGGCTGGGAGCGCGGTA

TCTTGAGTTTGAGGCCCTGGGATTCCTGAATGAGGACCATTGGGCTTCCAGGGAAAA

CTCAGGAGGAGGAGTGGAAGGCATTGGCTTACAATACCTAGGATATGTGATCAGAG

ACCTGGCTGCAATGGATGGTGGTGGATTCTACGCGGATGACACCGCTGGATGGGAC

ACGCGCATCACAGAGGCAGACCTTGATGATGAACAGGAGATCTTGAACTACATGAG

CCCACATCACAAAAAACTGGCACAAGCAGTGATGGAAATGACATACAAGAACAAA

GTGGTGAAAGTGTTGAGACCAGCCCCAGGAGGGAAAGCCTACATGGATGTCATAAG

TCGACGAGACCAGAGAGGATCCGGGCAGGTAGTGACTTATGCTCTGAACACCATCA

CCAACTTGAAAGTCCAATTGATCAGAATGGCAGAAGCAGAGATGGTGATACATCAC

CAACATGTTCAAGATTGTGATGAATCAGTTCTGACCAGGCTGGAGGCATGGCTCACT

GAGCACGGATGTGACAGACTGAAGAGGATGGCGGTGAGTGGAGACGACTGTGTGGT

CCGGCCCATCGATGACAGGTTCGGCCTGGCCCTGTCCCATCTCAACGCCATGTCCAA

GGTTAGAAAGGACATATCTGAATGGCAGCCATCAAAAGGGTGGAATGATTGGGAGA

ATGTGCCCTTCTGTTCCCACCACTTCCATGAACTACAGCTGAAGGATGGCAGGAGGA

TTGTGGTGCCTTGCCGAGAACAGGACGAGCTCATTGGGAGAGGAAGGGTGTCTCCA

GGAAACGGCTGGATGATCAAGGAAACAGCTTGCCTCAGCAAAGCCTATGCCAACAT

GTGGTCACTGATGTATTTTCACAAAAGGGACATGAGGCTACTGTCATTGGCTGTTTC

CTCAGCTGTTCCCACCTCATGGGTTCCACAAGGACGCACAACATGGTCGATTCATGG

GAAAGGGGAGTGGATGACCACGGAAGACATGCTTGAGGTGTGGAACAGAGTATGG

ATAACCAACAACCCACACATGCAGGACAAGACAATGGTGAAAAAATGGAGAGATG

TCCCTTATCTAACCAAGAGACAAGACAAGCTGTGCGGATCACTGATTGGAATGACC

AATAGGGCCACCTGGGCCTCCCACATCCATTTAGTCATCCATCGTATCCGAACGCTG

ATTGGACAGGAGAAATACACTGACTACCTAACAGTCATGGACAGGTATTCTGTGGA

TGCTGACCTGCAACTGGGTGAGCTTATCTGAAACACCATCTAACAGGAATAACCGG

GATACAAACCACGGGTGGAGAACCGGACTCCCCACAACCTGAAACCGGGATATAAA

CCACGGCTGGAGAACCGGGCTCCGCACTTAAAATGAAACAGAAACCGGGATAAAA

ACTACGGATGGAGAACCGGACTCCACACATTGAGACAGAAGAAGTTGTCAGCCCAG

AACCCCACACGAGTTTTGCCACTGCTAAGCTGTGAGGCAGTGCAGGCTGGGACAGC

CGACCTCCAGGTTGCGAAAAACCTGGTTTCTGGGACCTCCCACCCCAGAGTAAAAA

GAACGGAGCCTCCGCTACCACCCTCCCACGTGGTGGTAGAAAGACGGGGTCTAGAG

GTTAGAGGAGACCCTCCAGGGAACAAATAGTGGGACCATATTGACGCCAGGGAAAG

ACCGGAGTGGTTCTCTGCTTTTCCTCCAGAGGTCTGTGAGCACAGTTTGCTCAAGAA

TAAGCAGACCTTTGGATGACAAACACAAAACCACTGGGTCGGCATGGCATCTCCAC

CTCCTCGCGGTCCGACCTGGGCTACTTCGGTAGGCTAAGGGAGAAGGCGGCCGC
```

What is claimed is:

1. A chimeric yellow fever virus comprising a nucleic acid sequence encoding a Zika envelope (E) protein having the amino acid sequence of SEQ ID NO: 1.

2. The chimeric virus of claim 1 wherein the nucleic acid sequence encodes a Zika precursor membrane (prM) protein.

3. The chimeric virus of claim 1 capable of replication in a host cell or human subject.

4. The chimeric virus of claim 1 comprising a nucleic acid sequence having SEQ ID NO: 4 optionally comprising substitutions that provide synonymous codons.

5. A pharmaceutical composition comprising the chimeric virus of claim 1 and a pharmaceutically acceptable excipient.

6. A vaccine comprising the chimeric virus of claim 1 and an adjuvant.

7. A vector comprising a chimeric virus of claim 1.

8. The vector of claim 7 comprising a mammalian, human, insect, bacterial, plasmid, yeast, or retroviral gene.

9. A chimeric virus comprising a nucleic acid encoding a Zika envelope (E) protein having the amino acid sequence of SEQ ID NO: 1.

10. The chimeric virus of claim 9 wherein the nucleic acid sequence encodes a Zika precursor membrane (prM) protein.

11. The chimeric virus of claim 9 capable of replication in a host cell or human subject.

12. A pharmaceutical composition comprising the chimeric virus of claim 9 and a pharmaceutically acceptable excipient.

13. A vaccine comprising the chimeric virus of claim 9 and an adjuvant.

14. A vector comprising a chimeric virus of claim 9.

15. The vector of claim 14 comprising a mammalian, human, insect, bacterial, plasmid, yeast, or retroviral gene.

* * * * *